US011823796B2

United States Patent
McCrea

(10) Patent No.: US 11,823,796 B2
(45) Date of Patent: *Nov. 21, 2023

(54) DATA USAGE ALERTS

(71) Applicant: Comcast Cable Communications, LLC, Philadelphia, PA (US)

(72) Inventor: John McCrea, Palo Alto, CA (US)

(73) Assignee: Comcast Cable Communications, LLC, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/857,432

(22) Filed: Jul. 5, 2022

(65) Prior Publication Data

US 2022/0344042 A1   Oct. 27, 2022

Related U.S. Application Data

(63) Continuation of application No. 16/853,071, filed on Apr. 20, 2020, now Pat. No. 11,410,772, which is a
(Continued)

(51) Int. Cl.
| | |
|---|---|
| *G16H 40/67* | (2018.01) |
| *H04L 67/303* | (2022.01) |
| *H04H 60/65* | (2008.01) |
| *H04H 60/76* | (2008.01) |
| *H04L 67/50* | (2022.01) |

(Continued)

(52) U.S. Cl.
CPC ............ *G16H 40/67* (2018.01); *H04H 60/31* (2013.01); *H04H 60/65* (2013.01); *H04H 60/76* (2013.01); *H04L 43/16* (2013.01); *H04L 67/303* (2013.01); *H04L 67/535* (2022.05); *H04L 67/75* (2022.05); *A61B 5/0002* (2013.01); *G06F 2209/508* (2013.01); *G06Q 20/10* (2013.01); *G06Q 30/0201* (2013.01); *G06Q 30/0206* (2013.01); *H04L 41/509* (2013.01); *H04L 41/5032* (2013.01); *H04L 51/224* (2022.05);
(Continued)

(58) Field of Classification Search
CPC ............. G06F 11/3438; G06F 11/3476; H04L 63/102; H04L 45/3065; H04L 41/0631; H04L 67/22
See application file for complete search history.

(56) References Cited

U.S. PATENT DOCUMENTS

| | | |
|---|---|---|
| 6,643,355 B1 | 11/2003 | Tsumpes |
| 7,113,090 B1 | 9/2006 | Saylor et al. |

(Continued)

OTHER PUBLICATIONS

Arcelus et al., "Integration of Smart Home Technologies in a Health Monitoring System for the Elderly," IEEE, 2007, pp. 820-825.
(Continued)

*Primary Examiner* — Barbara B Anyan
(74) *Attorney, Agent, or Firm* — Banner & Witcoff, Ltd.

(57) ABSTRACT

Systems and methods for capturing and monitoring the health, safety, and/or activity of a user are described. In one aspect, the system generates a data usage pattern for the user and monitors the user's current data usage activity to detect data usage deviations from the user's usage pattern. When a deviation is detected, the system may send an alert message to the user or another user indicating that an anomaly may have occurred, permitting the user or another user to respond to the anomaly.

40 Claims, 11 Drawing Sheets

Related U.S. Application Data continuation of application No. 15/205,437, filed on Jul. 8, 2016, now Pat. No. 10,659,541, which is a continuation of application No. 13/606,069, filed on Sep. 7, 2012, now Pat. No. 9,419,735.

(51) Int. Cl.

| | | |
|---|---|---|
| *H04L 67/75* | (2022.01) | |
| *H04H 60/31* | (2008.01) | |
| *H04L 43/16* | (2022.01) | |
| *A61B 5/00* | (2006.01) | |
| *G06Q 30/0201* | (2023.01) | |
| *H04L 65/40* | (2022.01) | |
| *G06Q 20/10* | (2012.01) | |
| *H04L 41/50* | (2022.01) | |
| *H04L 51/224* | (2022.01) | |
| *H04M 3/22* | (2006.01) | |
| *H04M 15/00* | (2006.01) | |

(52) U.S. Cl.
CPC ........... *H04L 65/40* (2013.01); *H04M 3/2236* (2013.01); *H04M 15/85* (2013.01)

(56) References Cited

U.S. PATENT DOCUMENTS

| | | | |
|---|---|---|---|
| 7,783,666 B1 | 8/2010 | Zhuge et al. | |
| 7,873,074 B1* | 1/2011 | Boland | H04M 15/8214 370/468 |
| 8,014,273 B1* | 9/2011 | Barrett | H04L 41/0896 370/210 |
| 8,620,265 B1* | 12/2013 | Gailloux | H04M 15/85 379/114.03 |
| 8,700,464 B1 | 4/2014 | McAllister et al. | |
| 2002/0198985 A1 | 12/2002 | Fraenkel et al. | |
| 2004/0158573 A1* | 8/2004 | Bradley | G06F 16/221 707/999.102 |
| 2005/0216580 A1 | 9/2005 | Raji et al. | |
| 2006/0092010 A1 | 5/2006 | Simon et al. | |
| 2006/0252376 A1* | 11/2006 | Fok | H04M 3/2236 455/67.13 |
| 2007/0124244 A1 | 5/2007 | Mock et al. | |
| 2008/0208866 A1 | 8/2008 | Bhattacharjee et al. | |
| 2010/0017506 A1 | 1/2010 | Fadell | |
| 2010/0246401 A1* | 9/2010 | Woundy | H04L 12/2861 370/236 |
| 2010/0318647 A1* | 12/2010 | Savoor | H04L 12/14 709/224 |
| 2011/0035806 A1* | 2/2011 | Kramer | H04L 63/1441 709/248 |
| 2011/0060927 A1 | 3/2011 | Fillingim et al. | |
| 2011/0106946 A1* | 5/2011 | Bao | H04L 65/40 709/225 |
| 2011/0134983 A1* | 6/2011 | Mallya | H04L 47/26 375/225 |
| 2011/0301963 A1* | 12/2011 | Diab | H04N 21/632 725/40 |
| 2012/0054661 A1* | 3/2012 | Rados | H04L 43/0876 709/224 |
| 2012/0109716 A1 | 5/2012 | Giat et al. | |
| 2012/0158461 A1* | 6/2012 | Aldrey | G06Q 30/0242 705/7.29 |
| 2012/0226796 A1 | 9/2012 | Morgan | |
| 2012/0310838 A1 | 12/2012 | Harris et al. | |
| 2012/0311153 A1* | 12/2012 | Morgan | G06F 11/3438 709/226 |
| 2013/0073449 A1* | 3/2013 | Voynow | G06Q 30/0601 709/217 |
| 2014/0244057 A1* | 8/2014 | Hamouz | G06Q 50/06 700/291 |

OTHER PUBLICATIONS

GrandCare Systems—How-it-works, Overview, pp. 1-2, www.grandcare.com/page/how-it-works, last visited Feb. 6, 2012.

\* cited by examiner

DATA USAGE ALERTS

CROSS-REFERENCE TO RELATED APPLICATIONS

This application is a continuation of U.S. patent application Ser. No. 16/853,071 filed Apr. 20, 2020, which is a continuation of U.S. patent application Ser. No. 15/205,437 filed Jul. 8, 2016, now U.S. Pat. No. 10,659,541, which is a continuation of U.S. patent application Ser. No. 13/606,069 filed Sep. 7, 2012, now U.S. Pat. No. 9,419,735. The prior applications are each incorporated herein by reference in their entirety.

BACKGROUND

As the global population ages, more and more individuals choose to live independently at home, often without the aid of caregivers, such as family members, who can be there to notice problems when they arise. There remains a need, however, to maintain monitoring even in the absence of a caregiver, or when monitoring and/or oversight are unavailable.

SUMMARY

Some of the various features described herein relate to a system and method for storing a data (or device) usage (e.g., consumption) pattern for a user, the pattern identifying data/devices accessed by the user and a corresponding expected time of access indicator for the accessed data/device. The user's current data/device usage and a current time indicator may be compared with the pattern. In some aspects, the system and method may determine that the user's current data/device usage deviates from the user's data/device usage pattern, such as by a predetermined amount. In response to determining that the user's current data/device usage deviates from the user's data/device usage pattern, an alert may be sent to a device.

This summary is not intended to identify critical or essential features of the disclosures herein, but instead merely summarizes certain features and variations thereof. Other details and features will also be described in the sections that follow.

BRIEF DESCRIPTION OF THE DRAWINGS

Some features herein are illustrated by way of example, and not by way of limitation, in the figures of the accompanying drawings and in which like reference numerals refer to similar elements.

DETAILED DESCRIPTION

Figure 1:
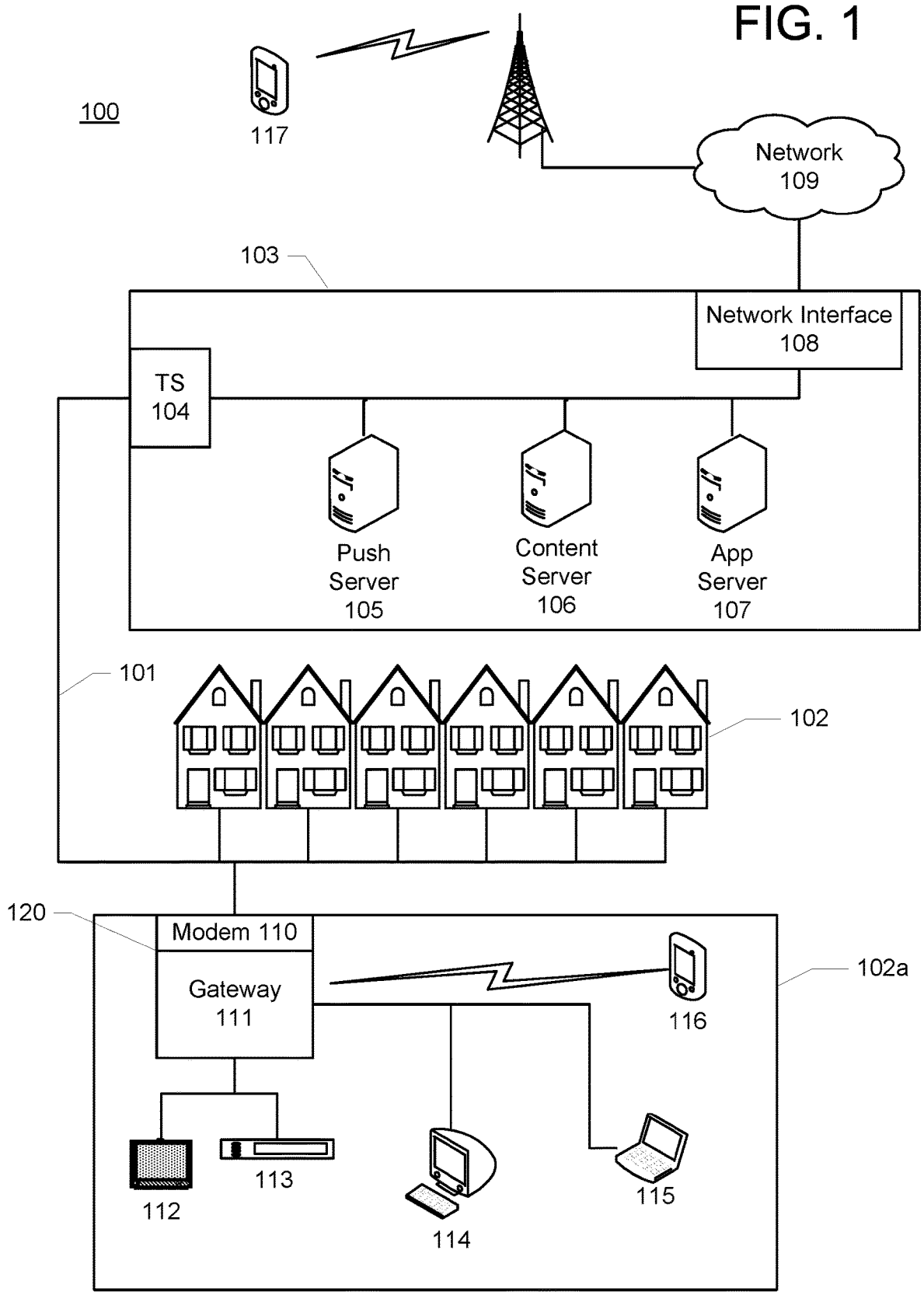
FIG. 1 illustrates an example information access and distribution network.

FIG. 1 illustrates an example information access and distribution network 100 on which many of the various features described herein may be implemented. Network 100 may be any type of information distribution network, such as satellite, telephone, cellular, wireless, etc. One example may be an optical fiber network, a coaxial cable network or a hybrid fiber/coax (HFC) distribution network. Such networks 100 use a series of interconnected communication links 101 (e.g., coaxial cables, optical fibers, wireless connections, etc.) to connect multiple premises, such as homes 102, to a local office (e.g., a central office or headend 103). The local office 103 may transmit downstream information signals onto the links 101, and each home 102 may have a receiver used to receive and process those signals.

There may be one link 101 originating from the local office 103, and it may be split a number of times to distribute the signal to various homes 102 in the vicinity (which may be many miles) of the local office 103. Although the term home is used by way of example, locations 102 may be any type of user premises, such as businesses, institutions, etc. The links 101 may include components not illustrated, such as splitters, filters, amplifiers, etc. to help convey the signal clearly. Portions of the links 101 may also be implemented with fiber-optic cable, while other portions may be implemented with coaxial cable, other links, or wireless communication paths.

The local office 103 may include an interface 104, which may be a termination system (TS), such as a cable modem termination system (CMTS), which may be a computing device configured to manage communications between devices on the network of links 101 and backend devices such as servers 105-107 (to be discussed further below). The interface may be as specified in a standard, such as, in an example of an HFC-type network, the Data Over Cable Service Interface Specification (DOCSIS) standard, published by Cable Television Laboratories, Inc. (a.k.a. CableLabs), or it may be a similar or modified device instead. The interface may be configured to place data on one or more downstream channels or frequencies to be received by devices, such as modems at the various homes 102, and to receive upstream communications from those modems on one or more upstream frequencies. The local office 103 may also include one or more network interfaces 108, which can permit the local office 103 to communicate with various other external networks 109. These networks 109 may include, for example, networks of Internet devices, telephone networks, cellular telephone networks, fiber optic networks, local wireless networks (e.g., WiMAX), satellite networks, and any other desired network, and the interface 108 may include the corresponding circuitry needed to communicate on the network 109, and to other devices on the network such as a cellular telephone network and its corresponding cell phones.

As noted above, the local office 103 may include a variety of servers 105-107 that may be configured to perform various functions. For example, the local office 103 may include a push notification server 105. The push notification server 105 may generate push notifications to deliver data and/or commands to the various homes 102 in the network (or more specifically, to the devices in the homes 102 that are configured to detect such notifications). The local office 103 may also include a data server 106. The data server 106 may be one or more computing devices that are configured to provide data to users in the homes. This data may be, for example, video on demand movies, television programs, songs, text listings, etc. The data server 106 may include software to validate user identities and entitlements, locate and retrieve requested data, encrypt the data, and initiate delivery (e.g., streaming) of the data to the requesting user and/or device.

The local office 103 may also include one or more application servers 107. An application server 107 may be a computing device configured to offer any desired service, and may run various languages and operating systems (e.g., servlets and JSP pages running on Tomcat/MySQL, OSX, BSD, Ubuntu, Redhat, HTML5, JavaScript, AJAX and COMET). For example, an application server may be responsible for collecting data such as television program listings information and generating a data download for electronic program guide listings. Another application server may be responsible for monitoring user viewing habits and collecting that information for use in selecting advertisements. Another application server may be responsible for formatting and inserting advertisements in a video stream being transmitted to the homes 102. And as will be discussed in greater detail below, another application server may be responsible for monitoring the data usage habits of an elderly person living at home alone.

An example home 102a may include an interface 120. The interface may comprise a device 110, such as a modem, which may include transmitters and receivers used to communicate on the links 101 and with the local office 103. The device 110 may be, for example, a coaxial cable modem (for coaxial cable links 101), a fiber interface node (for fiber optic links 101), or any other desired modem device. The device 110 may be connected to, or be a part of, a gateway interface device 111. The gateway interface device 111 may be a computing device that communicates with the device 110 to allow one or more other devices in the home to communicate with the local office 103 and other devices beyond the local office. The gateway 111 may be a set-top box (STB), digital video recorder (DVR), computer server, or any other desired computing device. The gateway 111 may also include (not shown) local network interfaces to provide communication signals to devices in the home, such as televisions 112, additional STBs 113, personal computers 114, laptop computers 115, wireless devices 116 (wireless laptops and netbooks, mobile phones, mobile televisions, personal digital assistants (PDA), etc.), and any other desired devices. Examples of the local network interfaces include Multimedia Over Coax Alliance (MoCA) interfaces, Ethernet interfaces, universal serial bus (USB) interfaces, wireless interfaces (e.g., IEEE 802.11), Bluetooth interfaces, and others.

Figure 2:
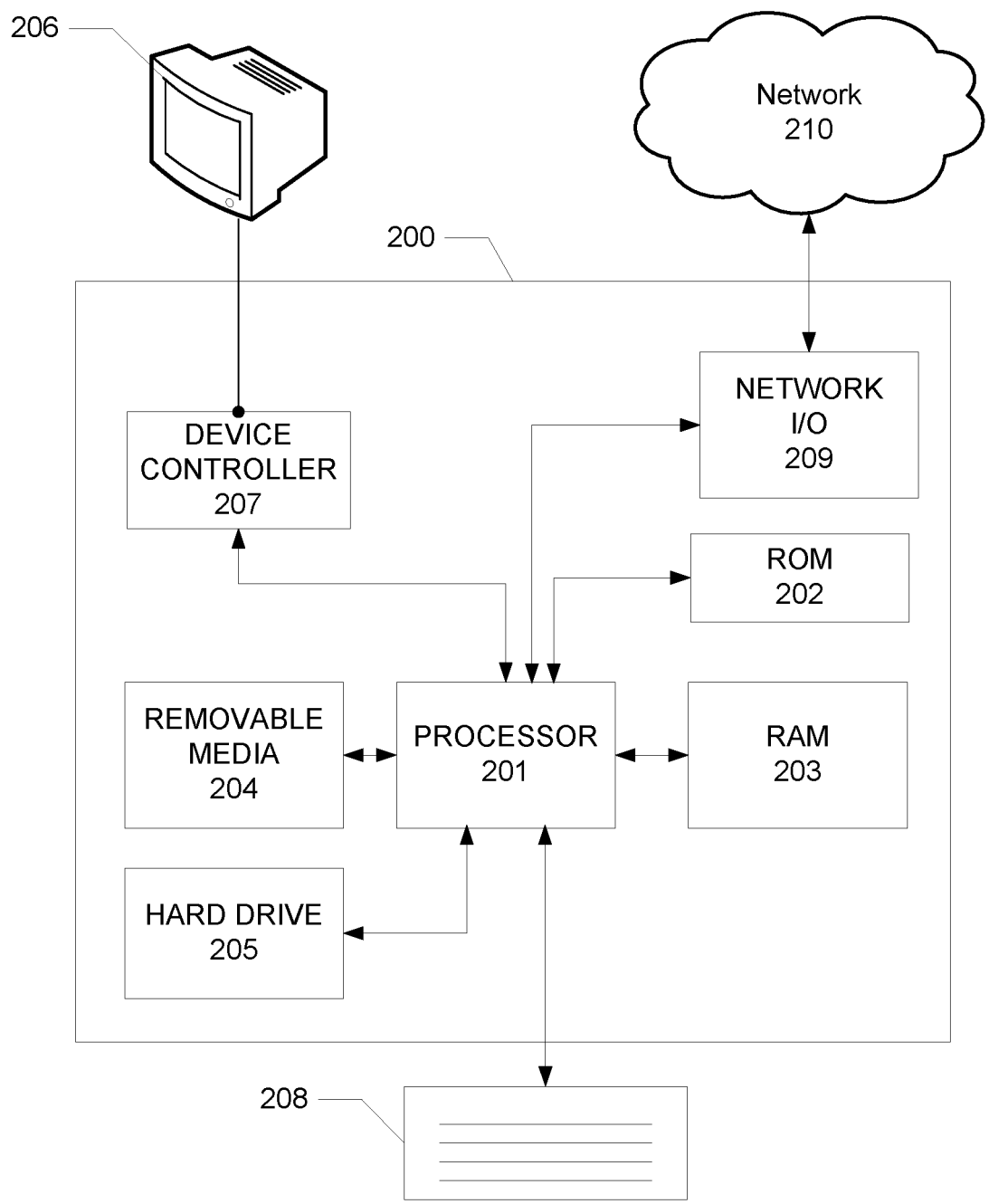
FIG. 2 illustrates an example hardware and software platform on which the various elements described herein can be implemented.

FIG. 2 illustrates general hardware and software elements that can be used to implement any of the various computing devices discussed herein. The computing device 200 may include one or more processors 201, which may execute instructions of a computer program to perform any of the features described herein. The instructions may be stored in any type of computer-readable medium or memory, to configure the operation of the processor 201. For example, instructions may be stored in a read-only memory (ROM) 202, random access memory (RAM) 203, hard drive, removable media 204, such as a Universal Serial Bus (USB) drive, compact disk (CD) or digital versatile disk (DVD), floppy disk drive, or any other desired electronic storage medium. Instructions may also be stored in an attached (or internal) hard drive 205. The computing device 200 may include one or more output devices, such as a display 206 (or an external television), and may include one or more output device controllers 207, such as a video processor. There may also be one or more user input devices 208, such as a remote control, keyboard, mouse, touch screen, microphone, etc. The computing device 200 may also include one or more network interfaces, such as input/output circuits 209 (such as a network card) to communicate with an external network 210. The network interface may be a wired interface, wireless interface, or a combination of the two. In some embodiments, the interface 209 may include a modem (e.g., a cable modem), and network 210 may include the communication links 101 discussed above, the external network 109, an in-home network, a provider's wireless, coaxial, fiber, or hybrid fiber/coaxial distribution system (e.g., a DOCSIS network), or any other desired network.

The system described herein may be used to monitor a user's data (e.g., content) usage, such as the user's consumption (e.g., viewing) activity, to detect deviations from the user's historical data usage pattern. A computing device (such as a computing device 200 located at local office 103 or home 102a) may track the user's data usage over a period of time and generate a data usage pattern for the user. Usage may be tracked for various devices, including data access devices (e.g., STBs, gateway devices, etc.), devices configured to display data, such as content (e.g., televisions, computers, portable devices, such as smartphones, etc.), and other devices. The tracked usage or data information may identify data volume (e.g., number of bytes of data uploaded, downloaded, or both combined per hour), direction (e.g., number of upload requests per hour, or number of download requests per hour), specific data (e.g., visits to a predetermined Internet web page, or viewing of video data such as television programs, on demand videos, etc.), devices used (e.g., a smart phone, tablet, computer, set-top-box, etc.), and one or more corresponding times of day for each expected usage.

These devices and other devices may be capable of functioning as both data access devices and display devices, such as a mobile phone that pulls content from the web and displays the content on its display or a television with a built-in data access device, like a receiver. The user's data usage pattern may be used to detect deviations in the user's data usage activity. For example, the computing device may monitor the user's present data usage and compare the usage to the user's historical pattern, which may indicate the user's expected data usage. If the monitored user normally watches the morning news and checks email for 20 minutes each weekday morning, but fails to do so, then the computing device may recognize this deviation. When the computing device determines that the user's present data usage deviates from the user's expected pattern (e.g., as stored in memory as the user's data usage history) by a predetermined amount, the computing device may send an alert of an anomaly to device(s) associated with the user and/or other users that may be caring for the user (e.g., a caregiver, a family member, a physician, etc.). By sending alerts, potential problems with the user (e.g., health, safety, and/or security issues) may be detected and signaled in order to protect the user. The devices, systems, and methods for monitoring user data consumption and detecting deviations may be part of and/or integrated with a total home solution, such as a home security system.

One or more devices installed in home 102a may be used to monitor the user's data usage and/or detect deviations from the user's pattern. For example, a user's viewing activity on a television 112 may be monitored for anomalies. Similarly, the user's viewing activity on personal computers 114, laptop computers 115, and/or wireless devices 116 may be monitored for anomalies. By utilizing devices (e.g., content service/display/access devices) that might already be installed at the user's home (e.g., television 112, STB 113, computer 114, etc.) to identify inconsistencies in the user's activity (including content consumption), the physical health, status, safety, etc. of users may be monitored without installing additional monitoring equipment, such as motion sensors, pressure sensors, and temperature sensors required in stand-alone health monitoring systems. In some embodiments, the monitoring may be performed by a gateway interface device, such as a cable modem or router, through which various other devices connect with one or more external networks. The gateway interface device may benefit from being a relatively centralized location within a home's data network, making monitoring of data traffic easier. In some embodiments, monitoring software may be loaded in to a cable modem's memory, and executed by a cable modem processor, therein requiring minimal additional installation effort. The monitoring may also be performed at one or more devices at local office 103 (e.g., one or more of the push server 105, content server 106, app server 107), within network 109, such as in a cloud network having distributed computing and/or data storage devices and/or functionalities, or any other device.

Figure 3:
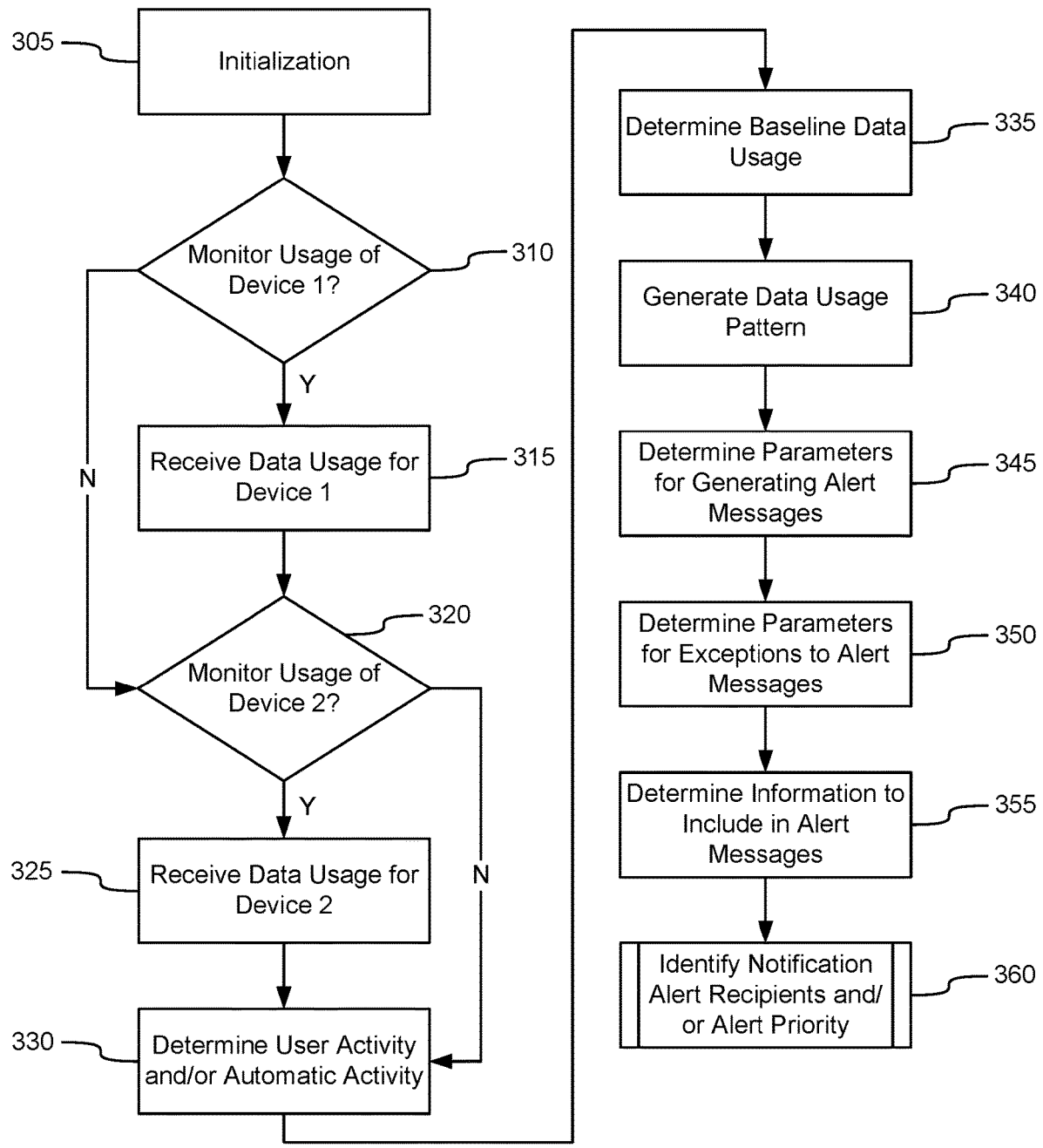
FIG. 3 illustrates an example method of configuring data according to one or more illustrative aspects of the disclosure.

FIG. 3 illustrates an example method of configuring a data usage deviation system according to one or more illustrative aspects of the disclosure. The method may be performed by any monitoring computing device, such as a personal computer in the home, the gateway or cable modem mentioned above, or any other device. In step 305, the computing device may perform initialization. Initialization may include identifying a user to monitor. For example, a user may indicate interest in being monitored and/or otherwise authorize collection of the user's data usage information for monitoring by indicating so via the user's account with the entity providing the monitoring service. The computing device may also automatically enroll the user for the monitoring service and provide the user an option to opt out of the service.

Initialization may also include, for example, a monitoring device at the user's home 102 (e.g., modem 110, gateway 111, STB 113, etc.) requesting and/or downloading monitoring software from central office 103 (e.g., from one of servers 105, 106, and/or 107). Software download may be performed in response to detecting that the user has signed up for the monitoring service, when the user has signed up for another service (e.g., data, telephone, television, etc.

service) from the entity providing the monitoring service, or when the monitoring equipment is installed at the home. Alternatively, the monitoring software may be preloaded on the monitoring device. Thus, when the monitoring device is installed at home 102, the monitoring device may begin collecting data usage information from the user's devices and/or from the user's profile as stored at, for example, central office 103 and monitoring for deviations as will be described in further detail in the examples below.

In steps 310 to 325, the computing device may identify various devices associated with the user to monitor. Some user devices may be better predictors of user activity than other devices. For example, the user's mobile phone may be a good predictor of user activity because the user may make and/or receive calls, use mobile applications (e.g., a game app, browser app, camera app, etc.), and/or send emails and text messages on the mobile phone. Other devices and/or activities that also rely on actual user input or interaction may also be good predictors of user activity. For example, the user pressing buttons on a television remote control or tuning to a particular channel on the user's STB may also be good indicators of user activity. Devices that might not be good predictors of user activity may be devices that primarily perform automatic activity. For example, a programmable thermostat, which may be connected to the same network as the monitoring device (e.g., the cable modem), may automatically adjust room temperatures based on the user's previous settings. Automatic adjusting of room temperatures often does not require direct user interaction (after the initial setup or occasional update). Thus, when programmable thermostats perform primarily automated activities, they might not be good indicators of user activity.

In step 310, the computing device may determine whether to monitor the usage of a first device, such as the user's television and/or STB. The user may specify the devices to monitor, such as via the user's account with the service provider. The user's account interface may include entry fields to indicate the devices to monitor. For example, the user may enter a unique identifier for each device to be monitored (e.g., a MAC address or name for a STB). The service provider may already have a list of the user's devices and corresponding unique identifiers. The user's devices may be indicated on a pre-populated list on the user's account, such as on a pull-down menu. The user may select the devices to be monitored using the pull-down menu. The devices may be listed separately on the user account interface with a corresponding user interface element (e.g., a radio button, check box, etc.) that permits the user to select or deselect devices to be monitored/not to be monitored. While user selection of devices to be monitored has been described using entry by the user, pull-down menus, radio buttons, and checkboxes, any means of selecting, updating, and/or deselecting devices to be monitored may be performed as would be readily recognized by one of ordinary skill in the art.

Additionally or alternatively, the computing device may automatically identify user devices to monitor. For example, the user's devices may be identified as primarily performing activities that require user interaction (e.g., a television, television remote control, a mobile phone, etc.) or as primarily performing automated activities that do not require user interaction (e.g., a programmable thermostat). The computing device may retrieve a list of device types (e.g., from central office 103) identified as user interaction devices or automated devices. The list may indicate, for example, mobile phones, STBs, televisions, remote controls, and PCs as user interaction devices. The list may also indicate, for example, programmable thermostats and digital clocks as automated devices. The computing device may determine which of the user's devices are user interaction devices and which are automated devices. The computing device may determine to monitor devices that are "user interaction devices" (step 310: Yes) and determine not to monitor devices that are "automated devices" (step 310: No).

The computing device may identify devices to monitor based on a combination of user input and automatic detection based on device type. For example, the user may indicate an interest in monitoring the user's mobile phone, such as via the user's account interface. The computing device may determine whether the user's mobile phone is a user interaction device. If the user's mobile phone is a user interaction device, the computing device may determine to monitor the mobile phone (step 310: Yes). If the user's mobile phone is not a user interaction device, the computing device may reject the user's request to monitor the mobile phone (step 310: No) and transmit a message to the user indicating the rejection. Alternatively, the computing device may transmit a message to the user indicating that the mobile phone is not a user interaction device and give the user the option to nevertheless monitor the mobile phone. If the user responds to the message indicating interest in monitoring the mobile phone, the computing device may determine to monitor the mobile phone (step 310: Yes).

If the first device is to be monitored (step 310: yes), the computing device may request and/or otherwise receive the user's data usage information for the first device in step 315. The computing device may receive the usage information from the first device. For example, the computing device may transmit a request for the usage information to the first device, and the first device may respond to the request with historical data usage information of the user on the first device. The first device may also send user activity updates to the computing device periodically or when they become available. Alternatively or additionally, the user's data usage information for the first device may be stored at another storage location, such as a local or networked storage location at home 102 or outside of the home, such as at central office 103 (e.g., in one of servers 105, 106, or 107) or elsewhere in network 109. Accordingly, the computing device may transmit a request for the usage information for the first device to central office 103 or network 109. One or more elements of central office 103 and/or network 109 may respond to the request with the requested data usage information. In some aspects, the data usage information for the first device may be stored as part of the user's data usage profile. For example, the service provider providing the monitoring service may also provide content recommendation services. Thus, if data usage information is collected for generating content recommendations for the user, the data usage information may also be used for the monitoring service.

If the first device is not to be monitored (step 310: no), the computing device may determine whether to monitor the usage of a second device in step 320. If the second device is to be monitored (step 320: yes), the computing device may receive data usage information for the second device in step 325. FIG. 3 illustrates obtaining user data usage information for two devices. However, data usage information may be collected for any number of sources and/or devices, such as the user's PC, mobile phone, STB, television, remote control, etc. Data usage tracked may include the user's content viewing habits, including the user's viewing activity on various devices (e.g., television 112, computer 114, etc.). As will be described in further detail in the examples below, the computing device may track programs and/or channels that the user tunes to, when various devices are turned on or off, and other interactions with the various devices. As described in the examples above, the user might be required to authorize collection of the user's data usage information before the computing device begins tracking the user's pattern.

The computing device may track and/or receive access information on the user's television 112 viewing patterns. For example, gateway 111 or modem 110 may receive television viewing data from television 112 or STB 113 and monitor the received data for deviations. Alternatively or additionally, the user's data usage may be transmitted to a computing device at local office 103 (e.g., push server 105, content server 106, app server 107, etc.) by each viewing or consumption device (e.g., TV 112, STB 113, PC 114, etc.), and the computing device at the local office 103 may perform the monitoring. The computing device (at home 102 or local office 103) may also track and/or receive data usage on the user's online (e.g., Internet) activity. As previously described, the user's data usage may be tracked across any device, including STBs, gateways, mobile devices, etc.

The computing device may track when the user signs onto a service provider account, such as an account provided by a television programming service provider, an internet service provider, a cellular service provider, etc. In some instances, the television service provider, the internet service provider, and/or the cellular service provider may be the same entity. The service provider(s) may provide the safety monitoring system that will be described in further detail in the examples below. The user may sign on to the service provider account by, for example, providing credentials (e.g., username, password, and/or other unique identifier) through a user interface. The interface may be a programming guide that displays program (e.g., television show, movie, etc.) schedules, a web browser, a webpage interface (e.g., a webpage associated with the service provider, such as a sign on webpage), an application window (e.g., a mobile application configured to run on a mobile device, such as a smartphone, or other device application interfaces), etc.

The user may also be signed on automatically, such as when the user powers on the television, STB, mobile phone, computer, etc. and a stored copy of the user's credentials is used to sign the user on. Thus, in some instances, powering on the television or STB may indicate a sign on activity. The user may also be signed on automatically when the user navigates to a sign on page (e.g., displayed at a webpage, program guide, etc.), opens an application window (e.g., a mobile application window, a PC application window, including a web browser, etc.), etc. The computing device may store, in the user's data usage pattern, timestamps indicating the time that the tracked activity (e.g., a sign on event) occurred. For example, the message transmitted by a user device to the computing device may indicate the activity, time of activity, and device that the activity occurred on (e.g., {SIGNON, 4:10 PM, STB1} if the user signs on to an account at 4:10 PM from the user's STB).

The computing device may similarly track the user's sign off activity. For example, the computing device may determine when the user signs off of the user's account and may store, in the user's data usage pattern, timestamps indicating the time that the tracked activity (e.g., a sign off event) occurred. Sign off events may occur, for example, when the user clicks a "sign off" or equivalent button, when the user powers off the television and/or STB, when the user navigates away from a page associated with the account (e.g., a user account webpage, a service provider webpage, an account page on a program guide, etc.), closes an application window, etc.

The computing device may also generate the user's data usage pattern based on many pieces of television viewing information, including television and/or programming access and access times associated with the television programming. For example, the computing device may determine when the television 112 or programming device associated with the television (e.g., STB 113) is powered on or off and generate and/or store a time indicator (e.g., a timestamp) for the power on or power off event in the user's data usage pattern. The message transmitted by a user device to the computing device may indicate the activity, time of activity, and device that the activity occurred on (e.g., {POWERON, 10:00 PM, TV2} if the user turns on the TV in the bedroom (TV2) at 10:00 PM). The computing device may similarly determine when the television or programming device associated with the television switches from a reduced-power state (e.g., a sleep state) to a normal state (e.g., a state that enables users to view programs, switch channels, etc.) or from a normal state to a reduced-power state. Time indicators for device state changes may be stored and/or used to generate the user's data usage pattern. For example, the message transmitted by a user device to the computing device may indicate the activity, time of activity, and device that the activity occurred on (e.g., {REDUCEDPWR-TO-NORMALPWR, 4:10 PM, TV1} if the TV in the user's living room (TV1) switches from reduced-power mode to a normal mode at 4:10 PM). In some instances, a change from a reduced-power state to a normal state may indicate a power-on (e.g., of a television, STB, etc.) event, and a change from a normal state to a reduced-power state may indicate a power-off event. In some instances, the computing device might track device power on and/or power off and state change events only while the user is signed on to an account associated with the monitoring system.

The computing device may also track the user's interactions with the television, the STB, a programming guide, particular programs, etc. The types of interactions tracked may include activity occurring between a power-on event and a power-off event. For example, the computing device may track the user's physical access commands with a television, STB, and/or remote control. Physical access commands include, but are not limited to, the user pressing (or otherwise actuating) buttons on the television and/or remote control (e.g., power buttons, number pad buttons, menu buttons, multifunction buttons, etc.), and the user providing voice commands provided to a television and/or remote control enabled to receive voice commands (e.g., a voice command to power on/off the television, a voice command to switch channels, etc.). The computing device may store, in the user's data usage pattern, timestamps indicating the time that the tracked activity (e.g., physical access commands) occurred. For example, the message transmitted by a user device to the computing device may indicate the activity, time of activity, and device that the activity occurred on (e.g., {CHANNELCHANGE, 4:10 PM, STB1} if the user switches channels on STB1 at 4:10 PM or {REMOTECONTROL, 7:00 AM, TV1} if the user uses a remote control to control TV1 in some way at 7:00 AM). In some instances, the computing device might track the user's physical interactions with the television and/or remote control only while the user is signed on to an account associated with the monitoring system.

The computing device may similarly track the user's interactions with a device (e.g., television, computer, mobile device, etc.) interface (e.g., a graphical user interface). For example, the computing device may track the user's interactions with a television programming guide. The computing device may also track the user's interactions with networked data, such as a webpage. For example, the computing device may track when the user accesses a webpage (e.g., navigates to the webpage) or leaves a webpage (e.g., navigates away from the webpage). The computing device may store, in the user's data usage pattern, timestamps indicating the time that the tracked activity (e.g., interactions with the interface, such as accessing the interface) occurred. For example, the message transmitted by a user device to the computing device may indicate the activity, time of activity, and device that the activity occurred on (e.g., {PROGRAMGUIDE, 4:10 PM, STB1} if any activity with the program guide provided by STB1 is detected at 4:10 PM or {EXITWEBPAGE1, 5:00 PM, PC1} if PC1 detects that the user has left webpage1 at 5:00 PM, such as by closing the web browser or browsing to another webpage). In some instances, the computing device might track the user's interactions with the interface only while the user is signed on to an account associated with the monitoring system.

The computing device may also track events of the user switching channels. In some instances, the computing device may track the average number of times that a user changes channels over a predetermined period of time. For example, if the computing device tracks the user's channel switching activity over a period of three days and determines that the user changed channels five times between 2 PM and 3 PM on Monday, six times between 2 PM and 3 PM on Tuesday, and seven times between 2 PM and 3 PM on Wednesday, the computing device might determine that the average number of times that the user changes channels from 2 PM to 3 PM is six times. The computing device may store, in the user's data usage pattern, timestamps indicating the observed time period (e.g., 2 PM to 3 PM) and the associated number of channel changes (e.g., 6). For example, the message transmitted by a user device to the computing device may indicate the activity, amount of activity, start time of activity, end time of activity, and device that the activity occurred on (e.g., {CHANNELSWITCH, 6, 2 PM, 3 PM, STB1} if the user switches channels on STB1 six times from 2 PM to 3 PM, on a particular day or on average). In some instances, the computing device might track the user's channel switching activity only while the user is signed on to an account associated with the monitoring system.

The computing device may also track specific channels that the user tunes to. For example, the user may typically tune to movie channel 1 at 8 PM on Tuesdays, and the computing device might store this activity in the user's data usage pattern. The stored activity information might include a unique identifier for movie channel 1 (e.g., a channel name, channel number, or other channel ID) and timestamp(s) indicating the time that the user tunes to movie channel 1. For example, the message transmitted by a user device to the computing device may indicate the activity, time and/or date of activity, and device that the activity occurred on (e.g., {MOVIECHANNEL1, 8:00 PM, TUES, STB1} if the user tunes to movie channel 1 at 8 PM on Tuesdays). In some instances, the computing device might track when the user switches to particular channels only while the user is signed on to an account associated with the monitoring system.

The computing device may also track instances of the user tuning to particular programs. The computing device may determine that the user tunes to a particular program by determining the time that the user tunes to a particular channel and determining whether the time that the user tunes to the channel is within a predetermined time period of a start time for the program. For example, if SEINFELD is scheduled to start on Mondays at 4 PM and the user tunes to the channel delivering SEINFELD within a predetermined time period (e.g., +/−10 minutes of 4 PM), the computing device may store the activity as an instance of tuning to SEINFELD. The computing device may store, in the user's data usage pattern, a unique identifier for the particular program (e.g., a program name, such as SEINFELD, a program identifier (PID), etc.) and timestamp(s) indicating the time that the user tunes to the particular program. For example, the message transmitted by a user device to the computing device may indicate the activity, time and/or date of activity, and device that the activity occurred on (e.g., {SEINFELD, 4:00 PM, MON, STB1} if the user tunes to SEINFELD on STB1 at 4 PM on Mondays or {SEINFELD, STB1} if the computing device knows that SEINFELD airs at 4 PM on Mondays, such as by accessing a programming schedule). In some instances, the computing device might track when the user switches to particular programs only while the user is signed on to an account associated with the monitoring system.

The computing device may also track instances of when the user schedules program recordings (e.g., to store at a DVR, at a network DVR, or at another local or network storage location). The computing device may also track instances of when the user requests data. Requests may include, for example, requests for specific content (e.g., television shows, movies, etc.) recorded by the user and/or other content directly available from the service provider (e.g., live or recorded streaming video and/or audio content, downloaded video and/or audio content, etc.). The computing device may store, in the user's data usage pattern, timestamps indicating the time that the tracked activity (e.g., scheduled program recordings and/or requests for data) occurred. For example, the message transmitted by a user device to the computing device may indicate the activity, time and/or date of activity, and device that the activity occurred on (e.g., {RECORDPROGRAM, 8:00 PM, DVR1} if the user schedules a program recording on DVR1 at 8:00 PM). In some instances, the computing device might track scheduled program recordings or requests for data only while the user is signed on to an account associated with the monitoring system.

The computing device may track and/or receive access information on the user's application activity, including the user's mobile application activity (e.g., an application on the user's mobile device, such as a smartphone). As previously described, the computing device may track the user's sign on and/or sign off activity. The computing device may also track when the user starts an application program (e.g., by opening an application window or otherwise initiating the application program to run) and/or ends the application program (e.g., by closing the application window or otherwise causing the application to stop running) For example, the computing device may determine that the user typically opens a crossword puzzle application on the user's device (e.g., a smartphone) at 8 AM on Saturdays and closes the application at 9 AM. The computing device may store, in the user's data usage pattern, timestamps indicating the time that the tracked activity (e.g., starting and/or ending an application) occurred. For example, the message transmitted by a user device to the computing device may indicate the activity, activity start time, activity end time, activity date, and device that the activity occurred on (e.g., {CROSSWORDAPP, 8:00 AM, 9:00 AM, SAT, SMARTPHONE} if on Saturdays the user opens a crossword app from the user's smartphone at 8:00 AM and closes it at 9:00 AM). In some instances, the computing device might track the user's application activity only while the user is signed on to an account associated with the monitoring system.

The computing device may collect the user's data viewing information for the various devices over a period of time (e.g., days, weeks, months, etc.). In step 330, the computing device may determine whether the various activities are user activity or automatic activity. User activity may include activity that generally requires initiation by the user (e.g., via user command or input). Any of the previously described activities received by the computing device (e.g., in steps 315 and 320) may be considered user activities. For example, switching channels on the user's STB is an example of user activity. Automatic activity, on the other hand, may include activity that occurs automatically, without user input or command. For example, the user's mobile phone may periodically pull emails, text messages, or other data from an external server without requiring a user command External servers may also automatically push data to the user's devices through a gateway at the user's home without user input. Similarly, the user's personal computer, laptop, etc. might receive automatic updates to various applications and/or operating systems. Recurring program recordings to a local storage device (e.g., a DVR) might also be automatic activity, such as when the user sets up periodic recordings for a TV series that runs every week.

The computing device may distinguish between user and automatic activity. The user may indicate which activity should be considered user activity via the user's service provider account. For example, the user may indicate switching channels on a STB, logging on to a service provider account on a mobile phone or PC, and powering on various devices as user activity. The computing device may identify all other activity as automatic activity. The computing device may also distinguish between user activity and automatic activity without user designation. Activities that occur at the same exact time each day of the week (or each week of the month, etc.) may be considered automatic activity. For example, if the operating system on the user's PC is configured to automatically download updates at 3 AM each Tuesday, the computing device may recognize the updates as occurring at exactly 3 AM each Tuesday and determine that the updates are automatic activity. The computing device may also query a database storing an activity list identifying activities as either user activity or automatic activity. The database may be stored, for example, at central office 103.

In step 335, the computing device may identify a baseline data usage. The baseline data usage may be, for example, the amount of automatic data usage averaged over a period of a day. The baseline data usage may also differ during each stage of the day. For example, if the user has scheduled recurring program recordings for several programs between 6 PM and 8 PM each day, the baseline data usage may be higher for the 6 PM to 8 PM timeframe than other times during the day.

In step 340, the collected information may be used to generate the user's data usage pattern, which may represent the user's expected data viewing pattern. The generated pattern may depend on specific types of data usage. For example, the computing device may determine that the user, on average, tunes to channel 1 at 6:05 PM by collecting data on the user's television activity over a period of weeks, months, etc., and store this activity in the user's data usage pattern. The computing device may similarly generate the pattern based on the user's other activity (e.g., mobile app usage, account sign on, etc.).

Additionally or alternatively, the computing device might not distinguish between different types of activity (e.g., account sign on/sign off activity, device power on/power off activity, the user's access commands, etc.), but instead determine the total amount of data used by one or more monitored devices. For example, the computing device might be gateway 111, modem 110, or any other device that interfaces various user devices with an external network (e.g., central office 103 and/or network 109). The interface device may track the amount of data transferred between the user's devices and the external network and generate the pattern based on the tracked amount of data. For example, the interface device may track the amount of data downloaded by the user devices from the network and/or uploaded by the user devices to the network.

Figure 9A:
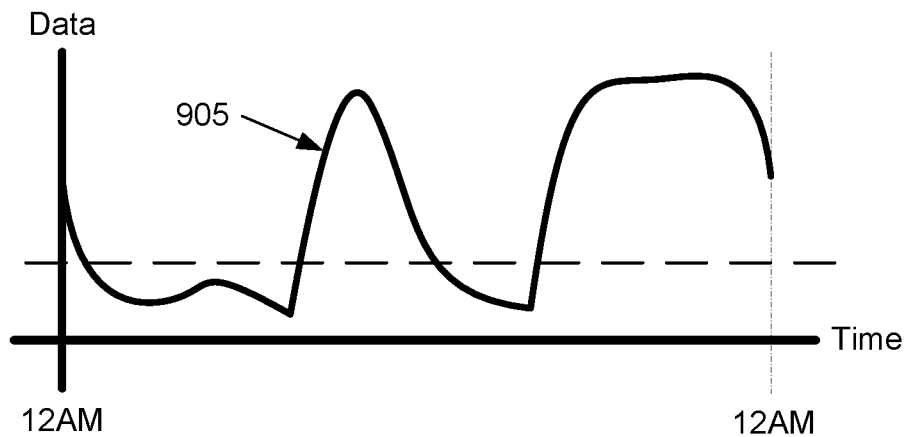
FIGS. 9A-C illustrate example data usage patterns according to one or more illustrative aspects of the disclosure.
Figure 9B:
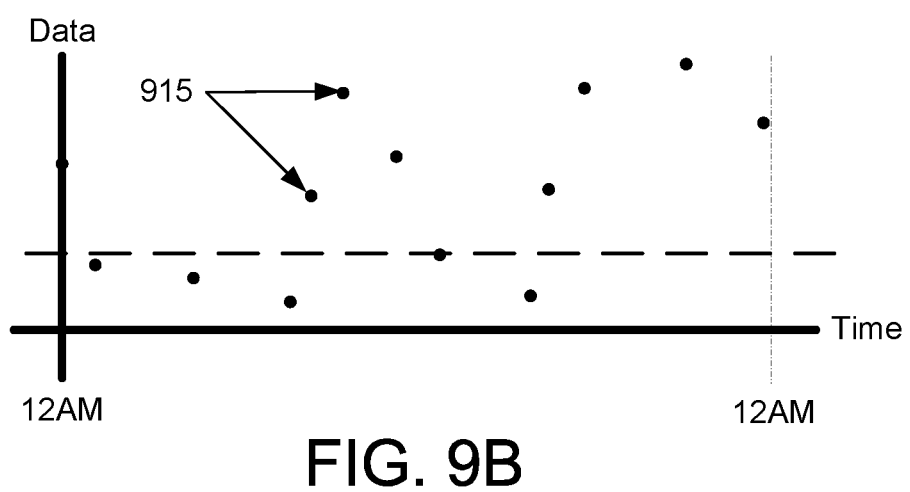
Figure 9C:
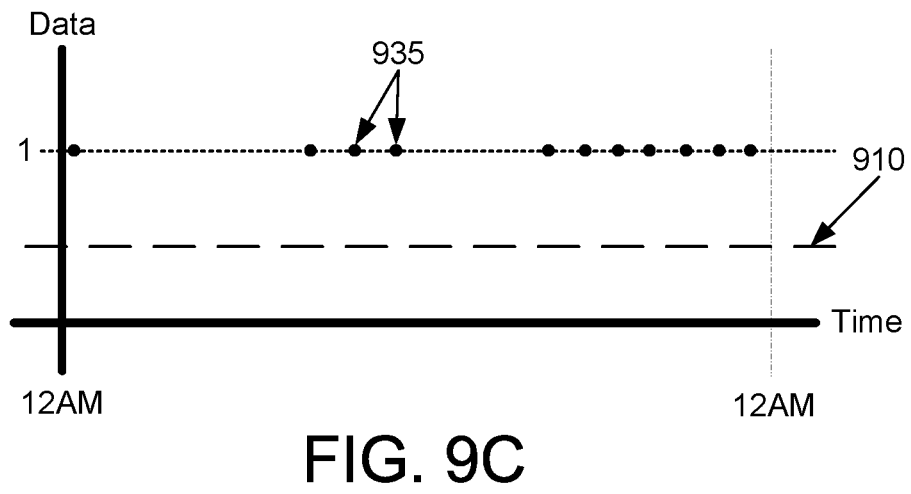

FIGS. 9A-C illustrate example data usage patterns generated and/or stored by the computing device according to one or more illustrative aspects of the disclosure. To generate the illustrated usage patterns, the computing device may determine the amount of data (e.g., in megabytes, gigabytes, etc.) that the user uses across all of the user's monitored devices. For example, as illustrated in FIG. 9A, the computing device may track the user's continuous data usage 905 over a period of a day. Additionally or alternatively, as illustrated in FIG. 9B, the computing device may identify discrete points 915 during the day that the user accesses data. The discrete points 915 may correspond to the continuous data graph of data usage 905 sampled at predetermined time periods (e.g., every ten minutes, thirty minutes, etc.).

Additionally or alternatively, as illustrated in FIG. 9C, the computing device might not track the amount of data used, but rather, track instances where the data usage is above a predetermined threshold. In some examples, the predetermined threshold may be the baseline data usage determined by the computing device in step 335. Because automatic activities generally do not require user input, the predetermined threshold may be the expected or average amount of data usage for the automatic activities (e.g., a baseline data usage as determined in step 335).

When the aggregate data usage of the user's devices is above the predetermined threshold 910, the computing device may indicate an expectation 935 that the user uses at least one device. For example, a "1" (or HI) may indicate that user activity is expected, whereas a "0" (of LOW) may indicate that user activity is not expected. The computing device may generate a continuous data usage pattern out of expectation points 935. Alternatively, the computing device may identify discrete points 935, as illustrated in FIG. 9C, of expected user activity over a period of a day. The computing device may sample (e.g., every 10 minutes, thirty minutes, etc.) a continuous data usage graph to identify discrete points 935. The daily data usage patterns of FIGS. 9A-C may be generated by tracking the user's data usage over a period of months, weeks, or years. The computing device may similarly generate data usage patterns for each day of the week.

In step 345, the computing device may determine various parameters for generating alerts. For example, the computing device may determine what constitutes a deviation from the user's expected data usage. Deviations may be based on a comparison of expected time of user activity and actual time of user activity.

Figure 10A:
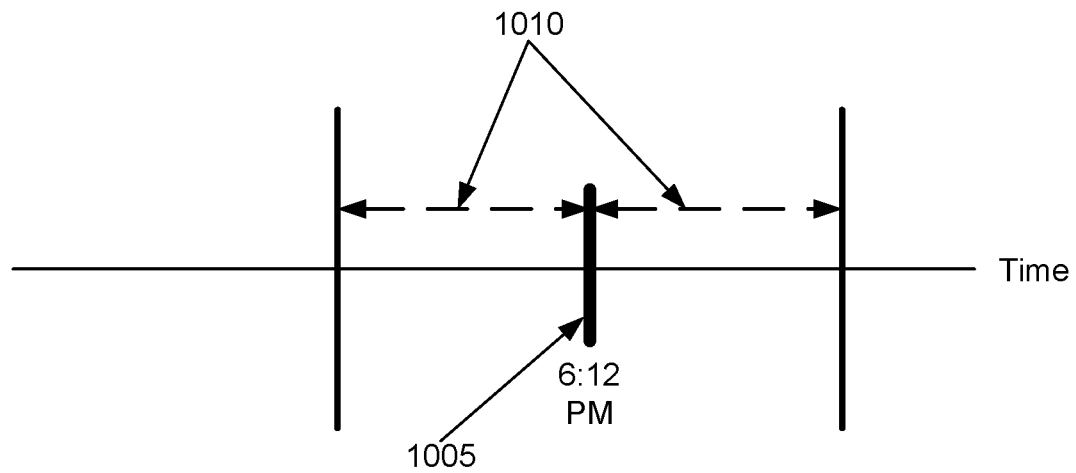
FIGS. 10A-B illustrate example time windows for detecting data usage deviations according to one or more illustrative aspects of the disclosure.

FIG. 10A illustrates an example time window for detecting data usage deviations according to one or more illustrative aspects of the disclosure. The user's pattern may indicate an expected activity 1005 at 6:12 PM. As previously discussed, the expected activity may be a specific type of activity (e.g., channel change, account sign on, etc.) or any activity. The computing device may be configured to provide a time buffer 1010 for the actual activity to occur. For example, the time buffer may be 15 minutes before and 15 minutes after 6:12 PM. If user activity is not detected between 5:57 PM and 6:27 PM, the computing device may determine that a deviation from the user's historical activity pattern has occurred. The time thresholds before and after the expected activity at 6:12 PM may be different. For example the time threshold before 6:12 PM may be 30 minutes and the time threshold after 6:12 PM may be 15 minutes. Thus, if user activity is not detected between 5:42 PM and 6:27 PM, the computing device may determine that a deviation has occurred.

Figure 10B:
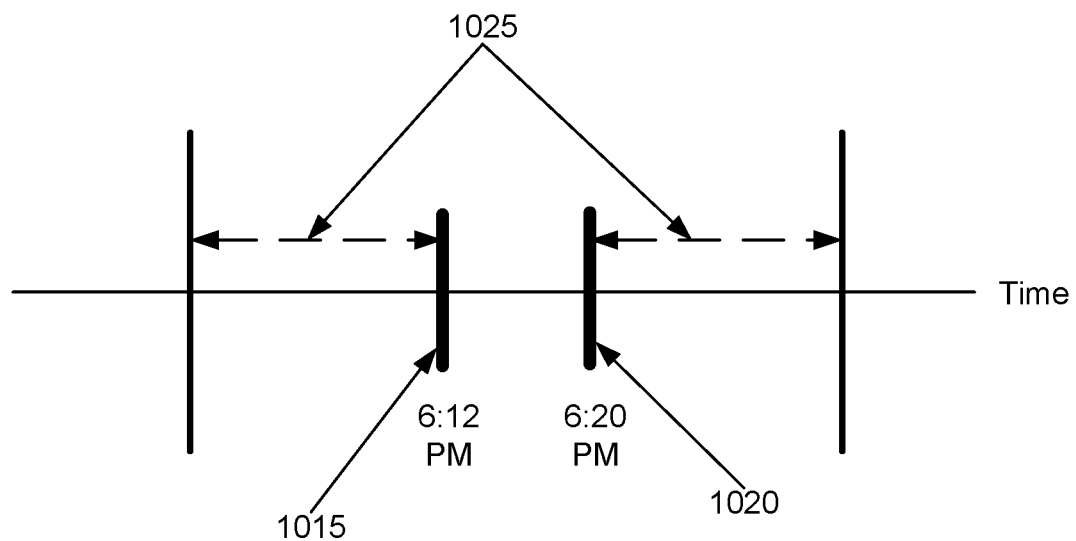

FIG. 10B illustrates another example time window for detecting data usage deviations according to one or more illustrative aspects of the disclosure. In some embodiments, two instances of user activity 1015 and 1020 may occur relatively close in time. For example, user activity may be close in time if they are within a predetermined time threshold. The time threshold may be the same or different from the threshold used as a time buffer for detecting actual user activity. For example, the time buffer 1025 may be 15 minutes. If two instances of user activity occur within 15 minutes of each other, the computing device may determine that the two instances occur relatively close in time. The computing device might generate a single time window to detect user activity based on the two instances of user activity. For example, the time window may be 15 minutes before the first expected activity 1015 and 15 minutes after the second expected activity 1020. In some embodiments, the computing device might expect at least two instances of user activity to occur between 5:57 PM and 6:35 PM. If at least two instances of activity do not occur during this time window, the computing device may determine that a deviation has occurred and generate a message (such as an alert message). In other embodiments, the computing device might expect at least one instance of user activity to occur during this time window. If at least one instance of activity does not occur during this time window, the computing device may determine that a deviation has occurred and generate an alert. In some examples, the time windows may be user configurable via the user's account. For example, the account interface may include entry fields for the user to provide various time thresholds as previously discussed.

In step 350, the computing device may determine parameters for generating exceptions to alerts. The monitored user (or other authorized notification recipients) may create exceptions to the monitoring. For example, if the monitored user knows that he or she will be traveling for the next four days, the user may turn off alerts for the next four days. The user may indicate these exceptions through the user's service provider account. The monitored user may also configure the computing device to stop sending alerts if a deviation has occurred, but the computing device has since detected user activity. For example, if user activity was expected between 6:15 PM and 6:30 PM, but no activity was detected, the computing device might nevertheless decide not to send an alert if user activity is detected at 6:35 PM and 6:35 PM is before the alert is sent. As another example, if the computing device expects one type of user activity, but detects a different type of user activity, the computing device might decide not to send an alert. For example, if the user's data pattern indicates a channel change between 5:45 PM and 6:15 PM, but instead detects use of a mobile app on the user's phone, the computing device may decide not to send an alert.

In step 355, the computing device may determine the information to be included in the alerts. In some instances, the alert to the monitored user or notification recipient might only indicate that a deviation has occurred. For example, an alert may state: "A deviation from FIRSTUSER's routine has occurred." In other instances, the alert might indicate that a deviation has occurred and also the time of the deviation. For example, if the first user failed to tune to Channel A at 7:00 PM as expected, the alert might state: "A deviation from FIRSTUSER's routine occurred at 7:00 PM." In additional instances, the alert might also indicate the specific anomaly. For example, if the monitored user failed to tune to SEINFELD at 7:00 PM as expected, the alert might state: "FIRSTUSER did not tune to SEINFELD at 7:00 PM as expected." The monitored user may configure the amount of information to provide in the alert messages to the second user by, for example, adjusting privacy settings on the user's account (e.g., by selecting one of the three options previously described).

Figure 4:
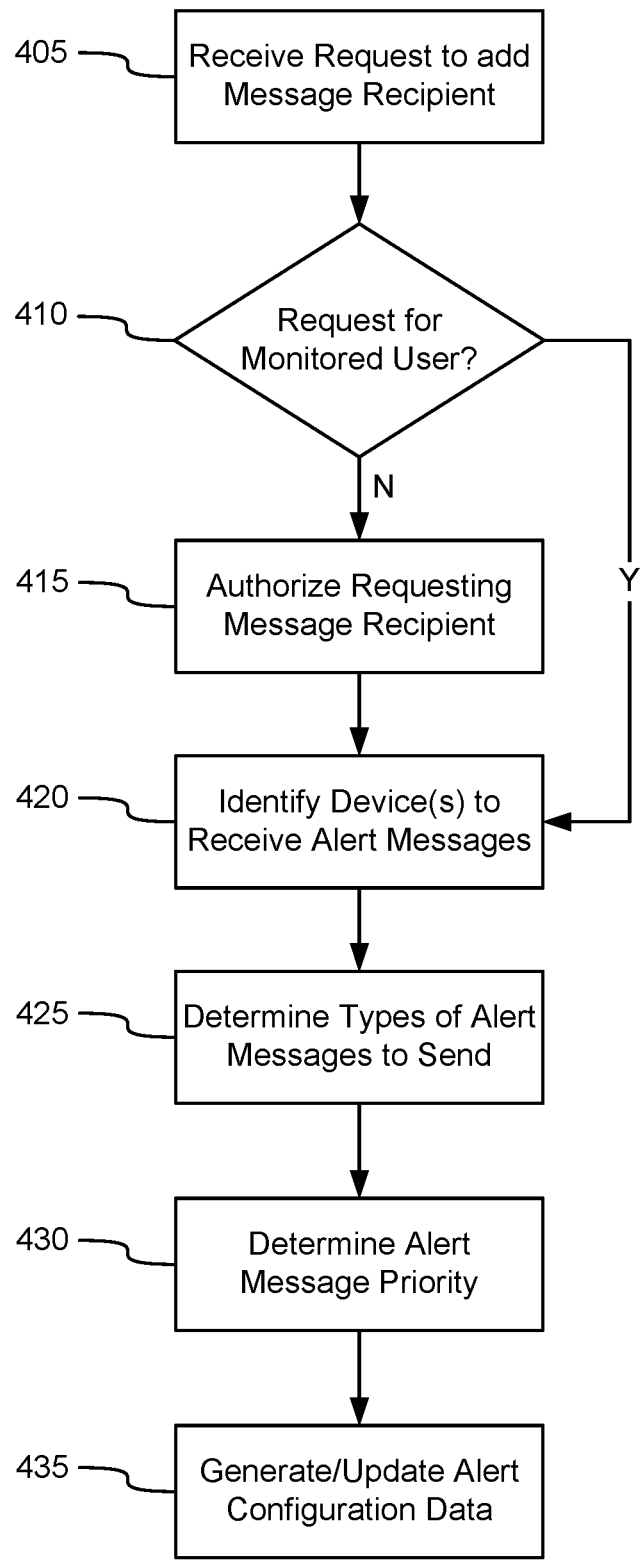
FIG. 4 illustrates an example method of configuring alerts according to one or more illustrative aspects of the disclosure.

In step 360, the computing device may identify notification recipients of alert messages and the order in which each notification recipient receives alert messages, as will be described in further detail with respect to FIG. 4. In step 405, the computing device may receive a request to add a message recipient (e.g., a recipient of alert messages). The message recipients may include the subject being monitored and/or other users caring for the subject being monitored (e.g., family members, caregivers, physicians, etc.). In step 410, the computing device may determine whether the request is to add the monitored user as a message recipient. For example, the computing device may determine that the request is for adding the monitored user if the request originated from the monitored user (e.g., via the monitored user's account) and/or indicates an identifier unique to the monitored user (e.g., an account name/number, email address, telephone number, etc.).

If the request is to add a user other than the monitored user as a message recipient (step 410: no) such as a caregiver, the computing device, in step 415, may attempt to authorize and/or authenticate the requesting message recipient. For example, a family member may input information identifying the monitored user, such as via a service provider account accessible by the family member. The family member may, for example, provide the service provider with the monitored user's email address, service provider account, or other unique identifier. The service provider may notify the monitored user that the family member requests authorization to receive messages on the monitored user's data usage deviations. If the monitored user authorizes the family member, such as by responding to the authorization request that the family member may receive messages, the computing device may configure the family member up as a message recipient.

In step 420, the computing device may identify devices to send messages to. The devices may be devices used, owned, or otherwise associated with message recipients if the message recipients have been authorized to receive messages. The monitored user may be preauthorized to receive messages (step 410: yes), whereas other message recipients may need to be authorized (e.g., in step 415). Messages may be transmitted to various devices, including wireless devices (e.g., cellular telephones, such as smartphones, and other mobile devices), computers (e.g., laptop computers, tablet computers, desktop computers, etc.), STBs and/or televisions.

In step 425, the computing device may determine the types of alerts to send. The types of alerts may depend on the types of devices assigned to receive the alert messages. For example, if a message recipient's PC is configured to receive messages, the computing device may send an email message. Alert messages may be of many other forms, including, but not limited to, text messages, messages displayed on an application or webpage, an email message, a message displayed on the television, such as a pop up message, a message on the program guide, etc. Alert messages may be push notifications from one or more service provide server, so that the recipient of the alert message might not need to periodically pull messages from the server. The message may also be a telephone call. For example, the computing device may initiate a telephone call to one or more designated devices, such as the user's mobile phone.

The devices to receive messages may be indicated with the request to add a user as a message recipient. For example, the monitored user may provide information identifying one or more devices to a service provider through the monitored user's account(s). The computing device may generate and/or otherwise provide a user interface having one or more entry fields that permit the monitored user to indicate the devices. For example, the monitored user may input the telephone number of his or her mobile phone into the user interface in order to receive text messages and/or telephone call alerts. The monitored user may similarly authorize one or more televisions and/or computers to receive messages by inputting identifiers for the televisions and/or computers (e.g., a computer name, a television name, IP address, MAC address, etc.). The monitored user may also authorize one or more email accounts and/or service provider accounts to receive messages by, for example, inputting email addresses or account identifiers (e.g., an account number) into the user interface. In some instances, the service provider account may be configured to receive messages when the monitored user signs onto the account and/or indicates that the account is authorized to receive messages (e.g., by checking an "alert me of problems" box). Any device capable of accessing the monitored user's email account and/or service provider account may then be authorized to access and/or receive messages. Requests from message recipients other than the monitored user may indicate devices to receive messages in a similar manner as that described above.

In step 430, the computing device may determine relative priorities among devices and/or message recipients to receive messages. For example, the monitored user, a first message recipient, and a second message recipient may be authorized to receive alert messages. The computing device may determine to send a first message to the monitored user and subsequently send a second message to the first message recipient if the monitored user does not respond to the first message. A third message may also be sent to the second message recipient, either simultaneously with the second message or after the second message (e.g., if the first message recipient does not respond to the second message). Thus, the monitored user may be prioritized above the first and second message recipients, and the first message recipient may be at the same level as or prioritized above the second message recipient.

The computing device may similarly determine relative priorities among various registered devices. For example, the computing device may be configured to transmit the alert message to the device that the monitored user was expected to use. For example, if the user's data usage pattern indicates that the user should have switched channels on the monitored user's television between 5:00 PM and 6:00 PM, the computing device may transmit the alert message for display on the television at 6:00 PM or a predetermined time thereafter (e.g., 6:05 PM). This feature may be beneficial if the monitored user watched television between 5:00 PM and 6:00 PM, but did not switch channels as expected, and thus the likelihood that the alert message will be read by the monitored user increases. In this example, the device that the monitored user was expected to use is prioritized over other devices.

The computing device may also be configured to transmit the alert message to the device(s) that the monitored user was not expected to use. For example, if the user's data viewing pattern indicates that the user should have signed on to the user's account on the user's television between 5:00 PM and 6:00 PM, the computing device may transmit the alert message for display on the user's computer and/or mobile phone or initiate an alert call to the user's phone. This aspect may be beneficial if the user is using another one of the user's devices (e.g., a computer or a mobile phone) instead of the device the user was expected to use (e.g., a television). This feature too may increase the likelihood that the user receives and/or reads the message in a timely manner. In this example, a device that the monitored user was not expected to use is prioritized over other devices.

The alert message may be configured to be transmitted to multiple devices (sequentially or simultaneously), such as all of the monitored user's devices and/or a message recipient's devices. Alert messages received by a device may be displayed on the device, such as on the user's television (e.g., as a scrolling or pop-up message on a programming guide), a computer (e.g., as a message displayed by an application on the computer or as a message transmitted to the user's email account), or a mobile device (e.g., as a text message).

In step 435, the computing device may store the alert configurations in an alert table. The alert table may include identifiers for authorized message recipients (e.g., the monitored user and other message recipients), devices associated with each authorized message recipient to receive messages, types of alerts to send to each device, and/or the message priorities (e.g., order of devices and/or message recipients to send messages to). The message configuration steps of FIG. 4 may be performed at any time and may be performed several times (e.g., if multiple users request to receive messages or if a user must renew the user's authorization to receive messages). In some embodiments, the computing device may perform one or more of these steps in response to receiving a request from the monitored user or a prospective message recipient.

Figure 5:
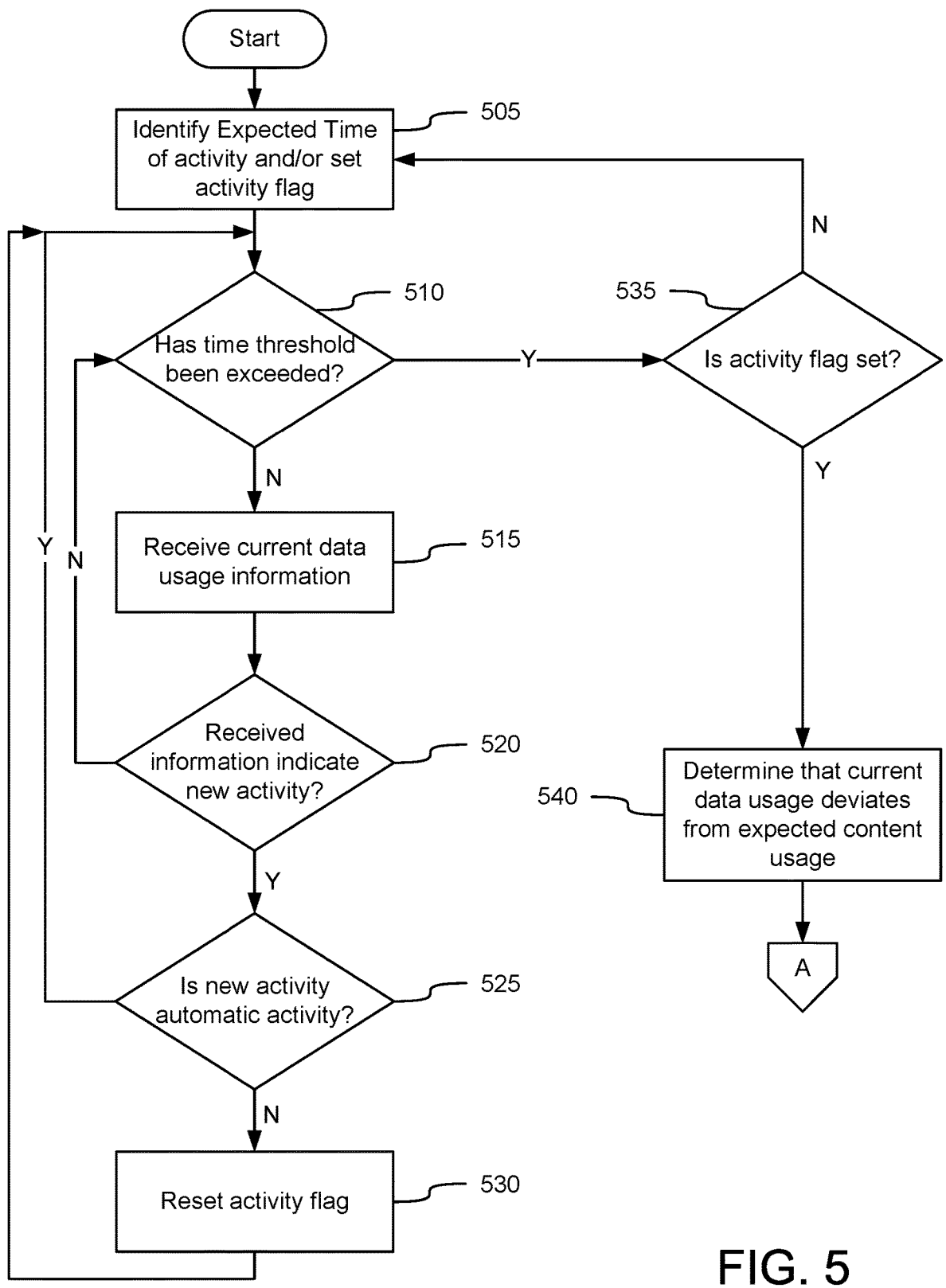
FIG. 5 illustrates an example method of monitoring according to one or more illustrative aspects of the disclosure.

FIG. 5 illustrates an example method of monitoring for a data usage deviation according to one or more illustrative aspects of the disclosure. The method may be performed by any monitoring computing device, such as a personal computer in the home, the gateway or cable modem mentioned above, or any other device. Generally, the computing device may compare the user's current data usage to the user's expected data usage pattern and/or determine whether the user's current data usage deviates from the expected data usage pattern by a predetermined amount. The comparison and determination may be based on one or more of the collected pieces of information stored as the user's data usage pattern.

In step 505, the computing device may identify an expected time of activity. The computing device may retrieve the next expected time of activity from the monitored user's stored data usage pattern. For example, if it is 6:00 PM, the computing device may search the user's data usage pattern for the next expected activity, which may be a channel change from the user's remote control, television, or STB at 6:20 PM. The computing device may also retrieve time threshold information from the data usage pattern or another database that stores configuration information (e.g., as determined and/or stored in step 345). For example, the computing device may determine that the threshold is +/−15 minutes, such that the computing device will watch for user activity between 6:05 PM and 6:35 PM. The computing device may also set an activity flag, the activity flag representing that activity is expected but has not yet occurred.

In step 510, the computing device may determine whether the time window (e.g., 6:20 PM+/−15 minutes) has passed. If the time is 6:13 PM, the computing device may determine that the current time is still within the time window (step 510: no). In step 515, the computing device may receive information on the user's current data usage (e.g., activity, time of activity, etc.). The information may be transmitted in a similar manner as previously described with respect to steps 315 and 325 (receiving information used to generate the user's usage pattern). For example, the computing device may query one or more monitored devices at a user location (e.g., devices within the user's home 102a or portable devices carried by the user within or outside home 102a) for current data usage information. The computing device may receive response messages from one or more devices. For example, as previously described, the computing device may receive a message, such as {SIGNON, 4:05 PM, STB1} indicating that the user signed on to the user's STB at 4:05 PM. The computing device may also receive one or more messages indicating all instances of user activity detected prior to the time of the request for current usage information and within a predetermined time frame. For example, the computing device may transmit a request for user activity at 6:13 AM. The request may also indicate a time window for activity, such as 6 hours from the time of the request (e.g., all user activity occurring between 12:13 PM and 6:13 PM), and ask the corresponding device to report all logged activity in that time window. In response to the request, the computing device may receive, from the user's device(s), a first message, {SIGNON, 4:05 PM, STB1}, and a second message, {POWERON, 3:00 PM, TV2}, if the devices at the user's home only detected 2 instances of activity occurring between 12:13 PM and 6:13 PM.

In some examples, the user's monitored device(s) may transmit message(s) indicating the user's current data usage activity without first receiving a request from a computing device at local office 103. A user device may transmit a message when it detects some form of user activity. For example, laptop computer 115 may transmit a message, {APPLICATIONOPEN, 8:13 PM, LAPTOP1}, when it detects that the user has opened (or otherwise initiated) an application on the user's laptop 1. A user device may also transmit a message when it does not detect user activity. For example, the user device may keep track of the user's expected activity (e.g., by storing a copy of the user's data usage pattern). When the user device determines that user activity was expected to occur at a particular time, but no user activity occurred at that time (or within a predetermined time threshold of that time), the user device may transmit a message indicating that no user activity occurred. A user device may also periodically transmit messages indicating user activity/non-activity to the computing device (e.g., every 5 minutes, every 10 minutes, etc.).

The requested current data usage information may be transmitted individually by each of the user's devices. For example, if user activity occurred at the user's TV 112 and STB 113, TV 112 and STB 113 may individually transmit, to the computing device, messages indicating the user's activity on each user device. Alternatively, information on the user's activity may be transmitted to the computing device by a shared device (e.g., a user device connected to each of the user's other devices, such as gateway 111).

In step 520, the computing device may determine whether the received information indicates any new activity. If no new activity has been received (step 520: no), the computing device may return to step 510 to determine whether the time window for detecting user activity has passed. If new activity has been received (step 520: yes), the computing device may determine, in step 525, whether the new activity is automatic activity or user activity. If the new activity is automatic activity (step 525: yes), the computing device may return to step 510 to determine whether the time window has passed. Alternatively (or additionally), the computing device may discard the received information identifying the automatic activity and/or request additional information identifying user activity from the device sending the original activity information or other devices associated with the user. For example, if STB 113 transmits user activity information that turns out to be automatic (e.g., initiated by the STB 113 and not the user), the computing device may request user activity information from a different STB in addition to (or instead of) STB 113. If the new activity is not automatic activity (e.g., is determined to be user activity), the computing device may reset the activity flag in step 530. Resetting the activity flag may indicate that user activity was detected during the time window identified in step 505. The computing device may distinguish between automatic and user activity as previously described above. For example, the computing device may determine whether the activity is automatic or user-generated based on an indication by the user in the user's account. The computing device may also query a database, such as one at central office 103, which identifies activities as either user-generated or automatic.

The computing device might not distinguish between types of activity (e.g., account sign on/sign off activity, device power on/power off activity, the user's access commands, etc.). For example, the computing device might determine (e.g., in step 505) that the next expected activity is a channel change from the user's remote control, television, or STB at 6:20 PM. However, the computing device might nevertheless reset the activity flag (e.g., in step 530) if the computing device detects any new user activity within the time window in steps 515-525. For example, the computing device may reset the activity flag if the computing device detects that the user powered on the user's television at 6:30 PM.

The computing device might distinguish between different types of activity. If activity A (e.g., a channel switching event) is expected at a particular time, the computing device may determine whether activity A occurs within a predetermined time window of the expected time. Thus, in some instances, the computing device might detect a deviation from the user's expected pattern if activity A does not occur within the predetermined time window, even if activity B (e.g., a device power on event) occurs within the predetermined time threshold. Activity B might be automatic activity and/or other activity that do not require user input. For example, activity B may be a lamp that is timed to turn on at 7 AM each morning.

In step 510, the computing device may determine that the time window has passed (step 510: yes). For example, if the time window spans from 6:05 PM to 6:35 PM, and the current time is 6:35 PM, the computing device may determine that the time window has passed. In step 535, the computing device may determine whether the activity flag is still set. If the activity flag is not set (e.g., has been reset), the computing device may determine that user activity was detected within the time window expecting user activity and return to step 505 to identify the next expected activity and a time for the next expected activity. If the activity flag is still set (step 535: yes), the computing device may determine, in step 540, that a deviation from the user's expected data usage pattern has occurred. In other words, the computing device may determine that a deviation (e.g., anomaly) occurs when activity is expected at a particular time or during a particular time frame (e.g., based on the user's expected data usage pattern), but no activity is detected within a predetermined time threshold of the expected time or within the expected time frame.

Additional examples of the computing device monitoring for and detecting an anomaly follow. The computing device may compare the time that the user signs on to a service provider account to the time that the user is expected to sign on to the account. Based on the comparison, the computing device may determine whether the user's current data usage deviates from the user's expected data usage by a predetermined threshold amount. For example, assume that the user's data usage pattern indicates that the user is expected to sign on to an account (e.g., via a GUI displayed on a device) at 5:05 PM and that the threshold is 15 minutes. If the user signs on at 5:10 PM, the computing device may determine that the user's current data usage does not deviate from the user's expected usage pattern. If, on the other hand, the user does not sign on by 5:20 PM, the computing device may determine that a deviation exists (e.g., in step 540).

Similarly, the computing device may determine deviations from expected sign off times. For example, assume that the user's data viewing pattern indicates that the user is expected to sign off at 7:00 PM and that the threshold is 15 minutes. If the user signs off of the account at 6:50 PM, the computing device might determine that the user's current data usage does not deviate from the user's expected usage pattern. If, on the other hand, the user does not sign off by 7:15 PM, the computing device may determine that a deviation exists (e.g., in step 540).

Device power on, power off, and/or state change activity may also be monitored to determine user anomalies. For example, the computing device may compare the time that the user's television is powered on to the time that the user's television is expected to be powered on (e.g., by comparing a current time to a timestamp stored in the user's data usage pattern that indicates the expected time of power on). Based on the comparison, the computing device may determine that the user's current data usage deviates from the user's data usage pattern by determining that the time that the user's television is activated deviates from the time that the user's television is expected to be activated by at least a predetermined threshold amount (e.g., in step 540). For example, assume that the user's data usage pattern indicates that the user is expected to activate the television at 5:05 PM and that the threshold is 15 minutes. If the user activates the television at 5:10 PM, the computing device might determine that the user's current data usage does not deviate from the user's expected usage pattern. If, on the other hand, the user does not activate the television by 5:20 PM, the computing device may determine that a deviation exists.

Similarly, the computing device may determine deviations from expected power off times. For example, assume that the user's data usage pattern indicates that the user is expected to power off the television at 7:00 PM and that the threshold is 15 minutes. If the user turns off the television at 6:50 PM, the computing device might determine that the user's current data usage does not deviate from the user's expected usage pattern. If, on the other hand, the user does not deactivate the television by 7:15 PM, the computing device may determine that a deviation exists (e.g., in step 540).

The user's physical access commands to a television, STB, remote control, and/or other devices (e.g., button presses, voice commands, etc.) may also be monitored to determine user anomalies. For example, the computing device may compare the time that a device (e.g., a television) expects to receive a command from the user to the current time and commands received at the current time. Based on the comparison, the computing device may determine (e.g., in step 540) that the user's current data usage deviates from the user's data usage pattern if the current time exceeds the expected time by a predetermined threshold amount, but no command from the user has been received by a device (e.g., the television).

The user's interactions with a graphical user interface (e.g., a programming guide, a webpage, etc.) may also be monitored to determine user anomalies. For example, the computing device may compare the time, as indicated in the user's data usage pattern, that the user is expected to access or leave a webpage to the current time and any user webpage accesses associated with the current time. Based on the comparison, the computing device may determine (e.g., in step 540) that the user's current data usage deviates from the user's data usage pattern if the current time exceeds the expected time by a predetermined threshold amount, but the computing device has not detected that the user accessed or left the webpage.

The frequency that the user switches program channels may also be monitored to determine user anomalies. For example, the computing device may compare the number of times that the user switched channels over a period of time to the expected number of times that the user switched channels as indicated in the user's data usage pattern. The computing device may detect a deviation from the user's data usage pattern (e.g., in step 540) if, for example, the user only switches channels one time between 2 PM and 3 PM on Tuesday and the usage pattern indicates that the user is expected to switch channels six times between 2 PM and 3 PM and a threshold for deviation is four channel switches. In some embodiments, the threshold may be six channel changes, and an anomaly may be detected if the user has no channel switching activity from 2 PM to 3 PM on a particular Tuesday.

The channels and/or programs that the user tunes to may also be monitored to determine user anomalies. For example, the computing device may compare the time that the user tunes to a particular channel and/or program to the time that the user is expected to tune to the particular channel and/or program. Based on the comparison, the computing device may determine (e.g., in step 540) that the user's current data usage deviates from the user's data usage pattern if the current time exceeds the expected time by a predetermined threshold amount, but the user has not tuned to the channel and/or program as indicated in the user's data usage pattern.

Data recording and/or data (e.g., content) requests may also be monitored to determine user anomalies. For example, the computing device may compare the time that the user records and/or requests content to the time that the user is expected to record and/or request content (e.g., as indicated in the user's data usage pattern). Based on the comparison, the computing device may determine that the user's current data usage deviates from the user's data usage pattern by determining that the time that the user records and/or requests content deviates from the time that the user is expected to record and/or request content by at least a predetermined threshold amount (e.g., in step 540). For example, assume that the user's data usage pattern indicates that the user is expected to request content at 8:00 AM and that the threshold is 20 minutes. If the user requests content at 7:50 AM, the computing device might determine that the user's current data usage does not deviate from the user's expected usage pattern. If, on the other hand, the user does not request content by 8:20 AM, the computing device may determine that a deviation exists.

The user's application access activity (e.g., accessing a mobile app) may also be monitored to determine user anomalies. For example, the computing device may compare the time that the user accesses any application on a mobile device (e.g., Application A, Application B, etc.) to the time that the user is expected to access an application (e.g., Application A). Based on the comparison, the computing device may determine (e.g., in step 540) that the user's current data usage deviates from the user's data usage pattern if the current time exceeds the expected time by a predetermined threshold amount, but the user has not accessed any application as indicated in the user's data usage pattern.

Because the system and method herein described monitors the user's data usage for deviations, the monitoring system may monitor the user's activity both while the user is inside of home 102*a* (e.g., when the user accesses data through STB 113) and while the user is outside of home 102*a* (e.g., when the user accesses a wireless device 116, such as a mobile phone, and/or an application included on the wireless device). For example, the user's data usage pattern may indicate that the user typically accesses a fitness workout mobile application between 6:00 AM and 7:00 AM. Accessing the fitness workout application may indicate, for example, that the user goes for walks outside the home from 6:00 AM and 7:00 AM. The computing device may determine that a deviation has occurred if the user does not access the fitness workout application between 6:00 AM and 7:00 AM. By monitoring the user's activity within and outside home 102*a*, the system and method herein described may provide more comprehensive health and safety monitoring for users (e.g., senior citizens) than standalone senior monitoring systems available only within home 102*a*.

Figure 6:
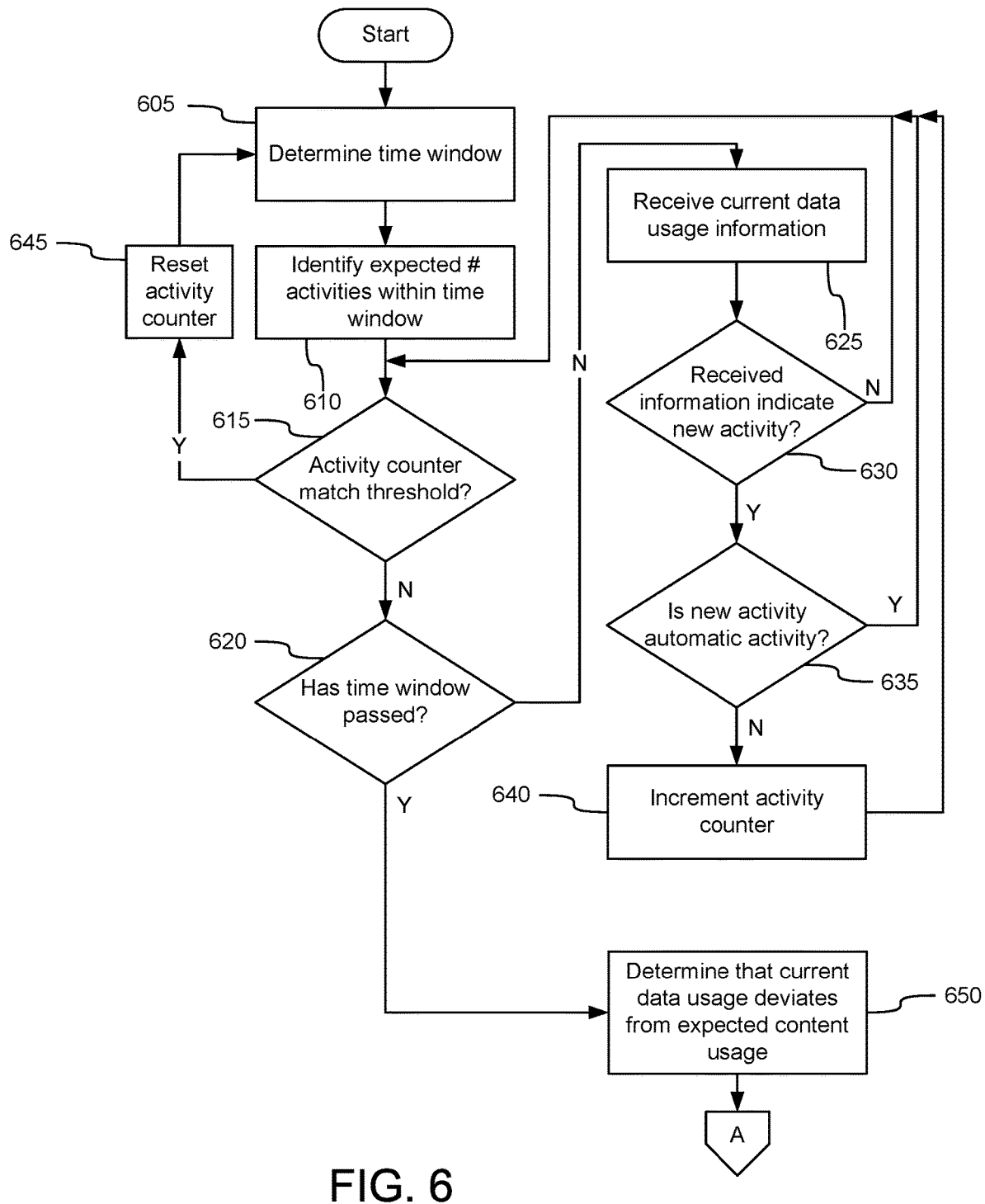
FIG. 6 illustrates another example method of monitoring according to one or more illustrative aspects of the disclosure.

FIG. 6 illustrates another example method of monitoring for a data usage deviation according to one or more illustrative aspects of the disclosure. The method may be performed by any monitoring computing device, such as a personal computer in the home, the gateway or cable modem mentioned above, or any other device. In step 605, the computing device may determine a time window for detecting anomalies. The computing device may query a database (e.g., an alert table) for a predetermined time window (e.g., a window of forty minutes).

Figure 11:
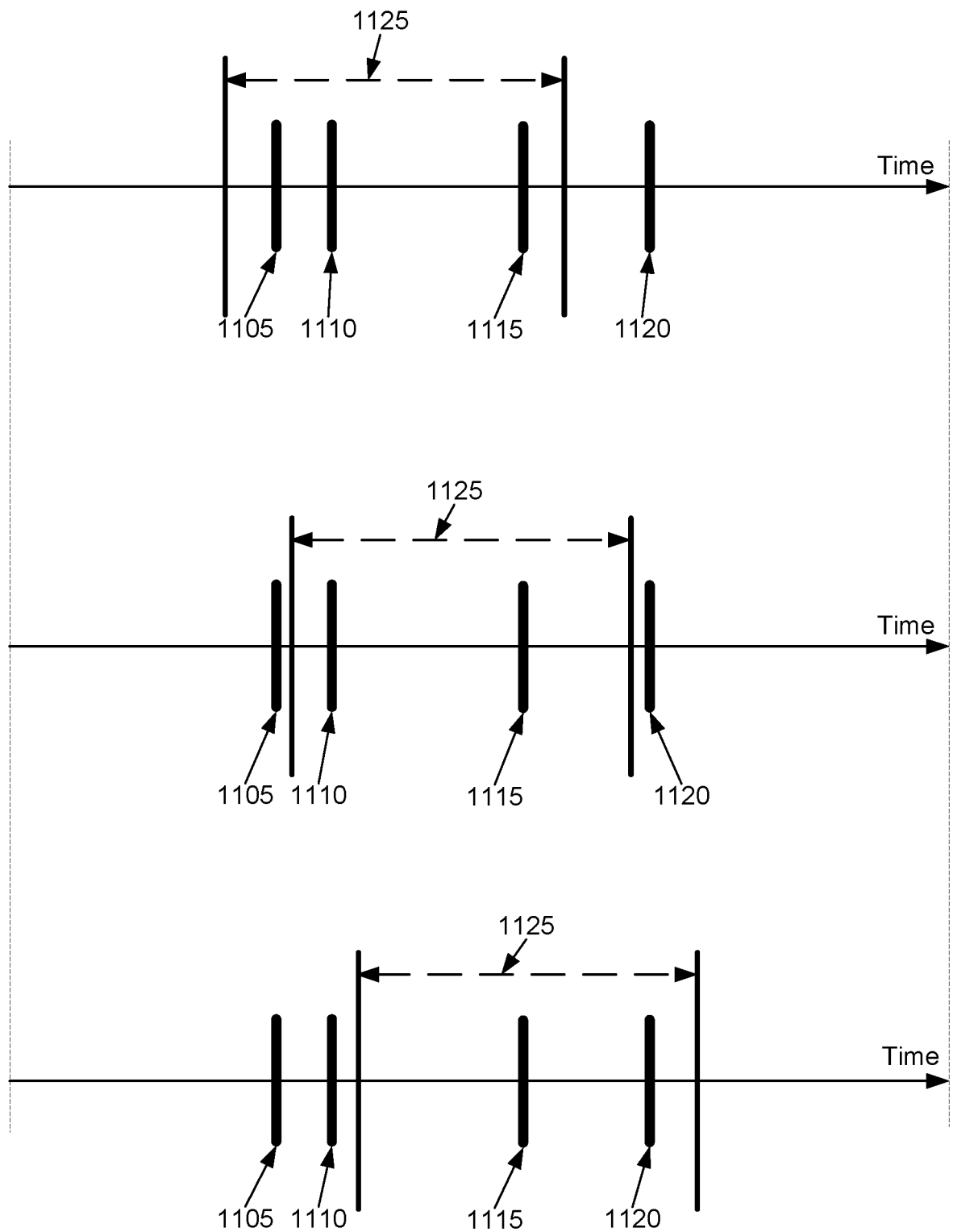
FIG. 11 illustrates additional example time windows for detecting data usage deviations according to one or more illustrative aspects of the disclosure.

FIG. 11 illustrates example time windows for detecting data usage deviations according to one or more illustrative aspects of the disclosure. The computing device may identify time window 1125 from the user's profile or other database. In step 610, the computing device may determine, from the user's data usage pattern, that three user activities 1105, 1110, and 1115 are expected to occur within the time window 1125. Another expected user activity 1120 may fall outside of time window 1125. The computing device may also determine a threshold number of activities for the computing device to determine that an anomaly has not occurred. In some embodiments, the threshold may match the number of expected user activities within the time window. For example, the computing device expects three user activities 1105, 1110, and 1115 to occur within time window 1125 and sets the threshold number of activities to three. In step 610, the computing device may also generate an activity counter to track the number of detected user activities within the time window. If the threshold number of activities matches the expected number of user activities during the time window, the computing device may set the initial activity counter to zero.

In other embodiments, the threshold might be different from the number of expected user activities within the time window. The threshold may be greater than the expected number of user activities. If the threshold is greater than the expected number of user activities, the computing device may set the activity counter to a number lower than zero. For example, if the expected number of user activities within the time window is three and the threshold is four, the computing device may set the activity counter to negative one.

The threshold may also be less than the expected number of user activities. A threshold less than the expected number during the time window may give the user, for example, one or more exceptions or free passes before an alert is sent. If the threshold is less than the expected number of user activities, the computing device may set the activity counter to a number greater than zero. For example, if the expected number of user activities within the time window is three and the threshold is two, the computing device may set the activity counter to one.

In step 615, the computing device may determine whether the activity counter matches the threshold number. If the activity counter does not match the threshold (step 615: no), the computing device may determine whether the time window has passed (e.g., that the current time is outside the time window) in step 620. If the current time is 6:30 PM and the time window is from 6:00 PM to 7:00 PM, the computing device may determine that the time window has not passed (step 620: no).

In step 625, the computing device may receive information on the user's current data usage (e.g., activity, time of activity, etc.). The information may be transmitted in a similar manner as previously described with respect to steps 515. For example, the computing device may query monitored devices for current data usage information and receive response messages from the monitored devices in response to the query. Alternatively or additionally, the monitored devices may transmit the user's current data usage information without a request from the computing device, such as when the user device detects user activity on the device or periodically transmit the user's data usage information.

In step 630, the computing device may determine whether the received data usage information indicates any new activity. If no new activity has been received (step 630: no), the computing device may return to step 615 to determine whether the activity counter matches the threshold number of activities. If new activity has been received (step 630: yes), the computing device may determine, in step 635, whether the new activity is automatic activity or user activity. If the new activity is automatic activity (step 635: yes), the computing device may return to step 615 to determine whether the activity counter matches the threshold number of activities. If the new activity is not automatic activity (e.g., is determined to instead be user activity), the computing device may increment the activity counter in step 640. Incrementing the activity counter may indicate that user activity was detected during the time window expecting user activity. The computing device may distinguish between automatic activity and user activity as previously described.

The computing device may return to step 615 to determine if the activity counter matches the threshold. If the activity counter matches the threshold (step 615: yes), the computing device may determine that a deviation during the time window has not occurred. The computing device may reset the activity counter in step 645. However, if the activity counter does not match the threshold (step 615: no) and the time window has passed (step 620: yes), the computing device may determine, in step 650, that a deviation from the user's expected data usage pattern has occurred. If a deviation occurs, the computing device might send one or more alerts for the deviation.

As previously described, the threshold may be less than the expected number of user activities. For example, as illustrated in FIG. 11, the computing device may expect three user activities 1105, 1110, and 1115 within time window 1125. However, the threshold for the computing device to determine that no deviation has occurred may be two out of the three expected user activities. Thus, the computing device may permit one missed activity. When the current time passes the expected time of the first user activity 1105 without detecting any current activity (as illustrated in the second time frame of FIG. 11), the computing device may excuse the first missed activity (e.g., not detect a deviation or send an alert). On the other hand, when the current time passes the second user activity 1110 without detecting any current activity (as illustrated in the third time frame of FIG. 11), the computing device may determine that a deviation has occurred because two deviations have occurred, but the user was permitted to be excused for only one deviation.

Figure 7:
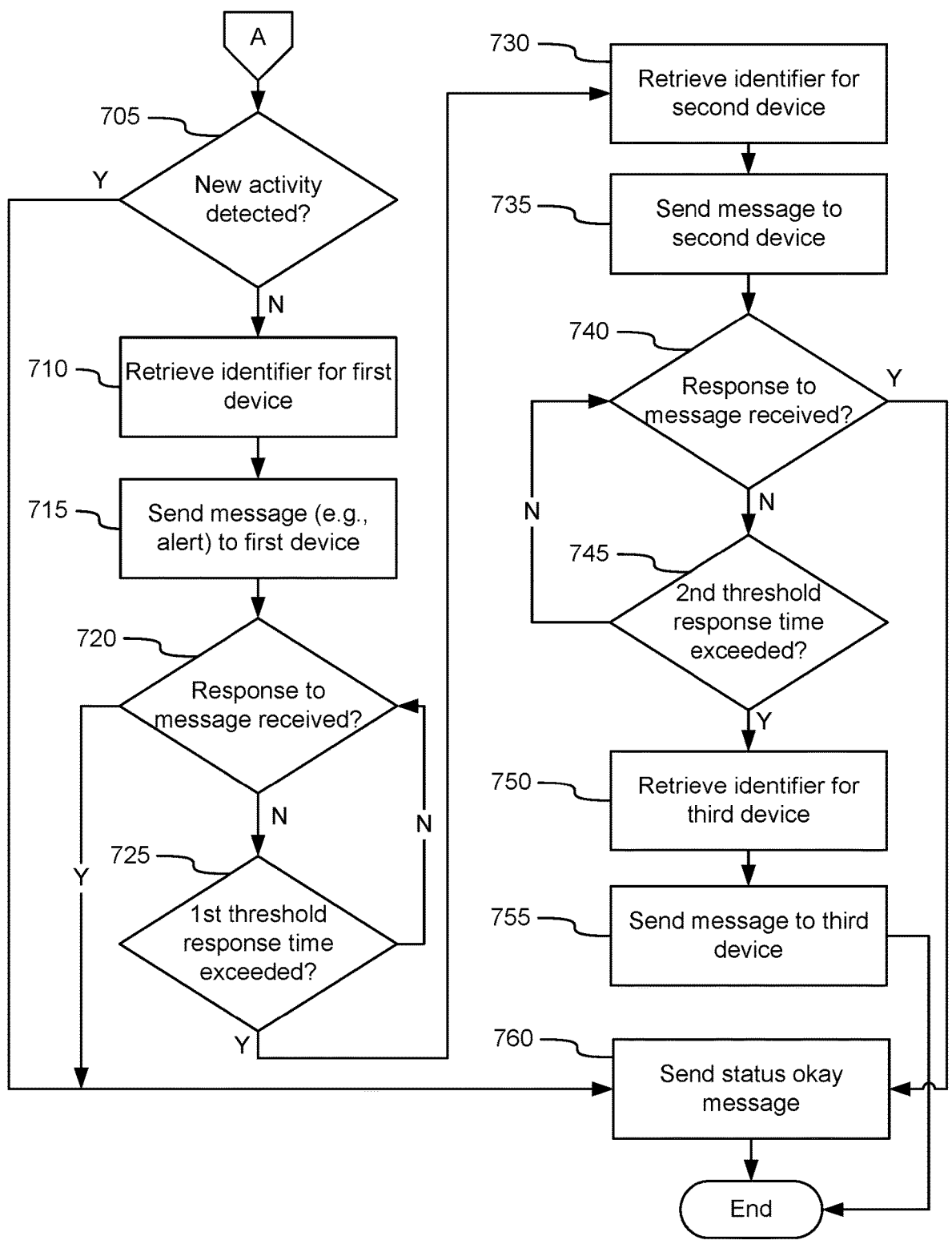
FIG. 7 illustrates an example method of sending alerts according to one or more illustrative aspects of the disclosure.

FIG. 7 illustrates an example method of sending alerts according to one or more illustrative aspects of the disclosure. The method may be performed by any monitoring device, such as a personal computer in the home, the gateway or cable modem mentioned above, or any other device. In step 705, the computing device may determine whether new user activity has occurred since identifying the deviation (e.g., in step 540 or 650). If new user activity has occurred (step 705: yes), the computing device may determine that the monitored user is okay (e.g., active) and send a message to one or more devices (e.g., the monitored user's devices or other message recipient's devices) indicating so in step 760. The computing device may perform step 705 at any point when determining whether and what alert messages to send. For example, if user activity is detected after a first alert message is sent to a device, the computing device may send a follow up status okay message to the device because new user activity has been detected.

In step 710, the computing device may retrieve an identifier from an alert table for a first device. As previously discussed, the alert table may store alert priorities. The alert table may indicate one of the monitored user's devices as the highest priority device (e.g., the user's mobile phone if mobile phone activity was expected). Thus, the computing device may retrieve an identifier for the first device (e.g., a telephone number of a mobile phone or MAC address of a television). The computing device may also retrieve information from the alert table indicating the type of alert to send to the first device. For example, the alert table may indicate that a phone call alert should be sent to the monitored user's mobile phone. The alert table may also indicate secondary alert types, such as a text message for the mobile phone. The secondary alert types may be used if the primary alert type cannot be sent.

In step 715, the computing device may send an alert message to the first device. In some instances, the computing device may attempt to contact the monitored user before contacting other message recipients. This feature may be beneficial when the monitored user (e.g., a senior citizen) deviates from an expected data usage because the monitored user has decided to deviate from the user's routine, not because there may be health or safety issues with the user. Thus, the message sent in step 715 may be sent to one or more devices associated with the monitored user. For example, the computing device may attempt to place an automated call to the monitored user's mobile phone. If the call fails (e.g., goes directly to a voicemail box without ringing, etc.), the computing device may attempt the secondary alert type, such as sending a text message. The computing device may also decide to make both a call to the mobile phone and send a text message to the mobile phone.

The computing device may also determine the amount of information to include in the alert message based on user settings in the alert table. For example, the alert message might only indicate that a deviation has occurred (e.g., "A deviation from FIRSTUSER's routine has occurred"), might indicate that a deviation has occurred as well as the time of the deviation (e.g., "A deviation from FIRSTUSER's routine occurred at 7:00 PM"), or might indicate additional specifics of the deviation (e.g., "FIRSTUSER did not tune to SEINFELD at 7:00 PM as expected").

In step 720, the computing device may determine whether a response (e.g., a return text message, a return call, a reply email message, a default return message, etc.) from the device(s) that was sent the first alert message has been received. If the computing device receives a response (step 720: yes), the computing device may determine that the monitored user is okay and send a status okay message in step 760. If the computing device has not received a response (step 720: no), the computing device, in step 725, may determine whether a first threshold response time period has passed. If a response has not been received within the first threshold time period (step 725: yes), the computing device may determine that the user's health and/or safety may be at risk. The first threshold time period may be, for example, 10 minutes. The time period may also be user-configurable. The monitored user may set and/or adjust the predetermined time period by, for example, signing on to the user's service provider account and adjusting the user's monitoring preferences.

In step 730, the computing device may retrieve an identifier from an alert table for a second device. The second device may be a second priority device. The computing device may also determine the type of alert to send to the second device. The type of alert may be indicated in the alert table, such as an email, account message, phone call, television pop-up, etc. In step 735, the computing device may send the alert message to the second device.

The second device may be associated with an authorized message recipient different from the monitored user. Alternatively, the second device may be another device associated with the monitored user. For example, if the first alert message was sent to a device the user was expected, but failed, to use during the time window (e.g., a television), the computing device may send the second alert message to another of the monitored user's devices, such as the user's mobile phone or PC. Thus, the monitored user may be given several chances to respond to alert messages before the computing device starts sending messages to other message recipients, such as caregivers and family members.

In step 740, the computing device may determine whether a response from the device(s) that were sent the second alert message (e.g., another one of the monitored user's devices) has been received. If the computing device receives a response (step 740: yes), the computing device may determine that the monitored user is okay and send a status okay message in step 760. If the computing device has not received a response (step 740: no), the computing device, in step 745, may determine whether a second threshold response time period has passed. If a response has not been received within the second threshold time period (step 745: yes), the computing device may determine that the user's health and/or safety may be at risk. The second threshold time period may be shorter than the first threshold time period, for example, 5 minutes.

If no response to the second message has been received (step 740: no) and the second time threshold has been exceeded (step 745: yes), the computing device may retrieve an identifier for a third device from an alert table in step 750 and send an alert message to the third device in step 755. The third device may be associated with a caregiver, family member, or other authorized message recipient. The computing device may send messages to any number of devices, simultaneously or sequentially based on information stored in the alert table. For example, if the alert table indicates a sequence of five devices to send alert messages to, the computing device may send five alert messages in sequence as described with respect to FIG. 7. In some embodiments, the final message may be sent to a caregiver or emergency responders (e.g., a 911 call). If an alert message is sent to one of the monitored user's devices, the computing device may wait a predetermined amount of time for a response (e.g., steps 725 and 745) from the user before sending the next message. If a message is sent to an alert recipient different from the monitored user, the computing device might not wait for a response from the message recipient before sending additional messages (e.g., to emergency responders).

Figure 8:
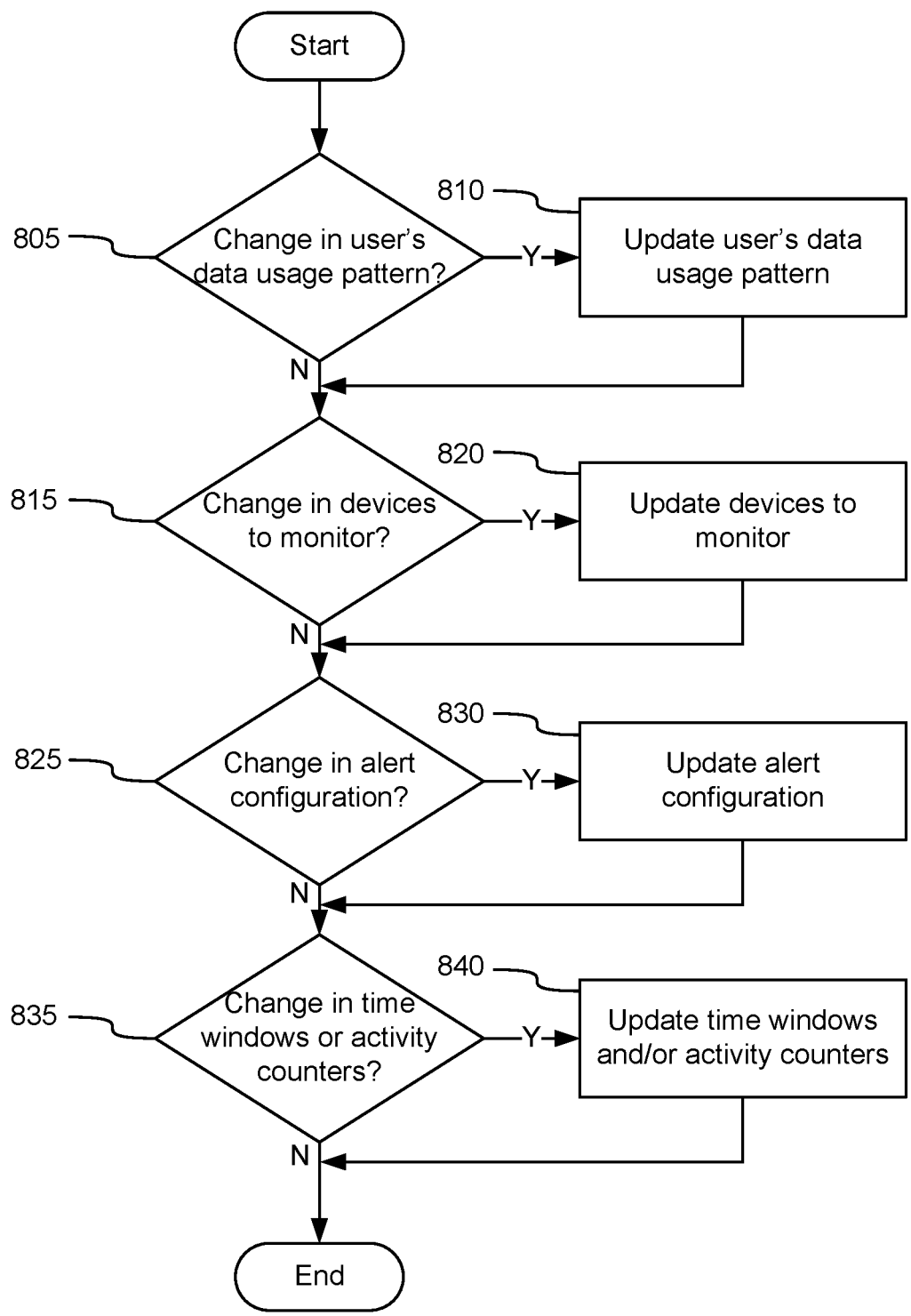
FIG. 8 illustrates an example method of updating data according to one or more illustrative aspects of the disclosure.

FIG. 8 illustrates an example method of updating data usage deviation system parameters according to one or more illustrative aspects of the disclosure. The method may be performed by any monitoring computing device, such as a personal computer in the home, the gateway or cable modem mentioned above, or any other device.

In step 805, the computing device may determine whether a change in the user's data usage pattern has occurred. If a change has occurred (step 805: yes), the computing device may update the user's data usage pattern in step 810. For example, the computing device may periodically update the user's data viewing pattern by receiving additional (e.g., updated) information on the user's data viewing habits and factoring the habits into the user's current data viewing pattern. The computing device may also update the user's data viewing pattern at irregular periods, such as in response to detecting multiple deviations from the pattern. For example, the user's data usage pattern may indicate that the user typically tunes to channel A at 2 PM on Tuesdays. If over a predetermined period of time (e.g., over a period of three weeks), the computing device detects that the user tunes to channel B at 2:55 PM on Tuesdays, the computing device may update the user's data usage pattern (e.g., by indicating the user's expected viewing time for channel A to be 2:55 PM, indicating the user's expected viewing time to be a weighted average time between 2 PM and 2:55 PM, etc.). Thus, based on heuristics, pattern modeling, etc., the computing device may keep the user's data usage pattern up-to-date based on changes to the user's activity.

In step 815, the computing device may determine whether there is a change in the user's devices to monitor. A change may occur if the user adds or removes one or more monitored devices via the user's account. A change may also occur if one or more devices connect to the monitoring device (e.g., a gateway interface) or disconnect from the monitoring device for an extended period of time (e.g., weeks, months). If a change in devices is detected (step 815: yes), the computing device may update the list of user devices to monitor in step 820.

In step 825, the computing device may determine whether a change in alert configuration has occurred. Changes in alert configurations include, for example, changes in the message recipients to receive alert messages (e.g., a removal or addition of one or more message recipients), changes in devices to receive messages, changes in the types of alerts to send to send to the devices, changes in device and/or user alert priority, and changes to the type of information to include in the alert messages. If a change in alert configurations is detected (step 830: yes), the computing device may update the alert configurations in step 830 (e.g., by modifying an alert table).

In step 835, the computing device may determine whether a change in time windows, thresholds, and/or activity counters has changed. If a change in time windows, time thresholds, and/or activity counters has changed (step 835: yes), the computing device may update the time windows, time thresholds, and/or activity counters in the monitored user's profile in step 840. For example, a time window of +/−15 minutes may be updated to a time window of +/−5 minutes if desired by the monitored user, caregivers, family members, etc. They may indicate the new time window via an account with the service provider.

The various features described above are merely non-limiting examples, and can be rearranged, combined, subdivided, omitted, and/or altered in any desired manner. For example, features of the computing device described herein (which may be one of servers 105, 106, and/or 107) can be subdivided among multiple processors and computing devices. The true scope of this patent should only be defined by the claims that follow.

What is claimed is:

1. A system comprising:
a gateway device configured to send data indicating first internet data usage associated with a user device during a first time period; and
a computing device, wherein the computing device comprises:
one or more processors; and
memory storing instructions that, when executed by the one or more processors, cause the computing device to:
receive, from the gateway device, the data;
determine that the first internet data usage is less than, by at least a threshold, second internet data usage associated with the user device during a second time period, wherein the second time period occurs prior to the first time period; and
based on determining that the first internet data usage is less than, by at least the threshold, the second internet data usage, send an alert message to a second computing device.

2. The system of claim 1, wherein the second internet data usage comprises one or more of internet activity associated with the user device or application software activity associated with the user device.

3. The system of claim 1, wherein:
the second internet data usage comprises activation of a display device associated with the user device during the second time period, and
the instructions, when executed by the one or more processors, cause the computing device to determine that the first internet data usage is less than, by at least the threshold, the second internet data usage by determining that the display device was not activated during the first time period.

4. The system of claim 1, wherein:
the second internet data usage comprises signing on to a service provider account associated with the user device during the second time period, and
the instructions, when executed by the one or more processors, cause the computing device to determine that the first internet data usage is less than, by at least the threshold, the second internet data usage by determining that a sign on to the service provider account did not occur during the first time period.

5. The system of claim 1, wherein the instructions, when executed by the one or more processors, cause the computing device to determine that the first internet data usage is less than, by at least the threshold, the second internet data usage by determining that data has not been accessed by the user device within the first time period.

6. The system of claim 1, wherein the first time period and the second time period occur during a common time range on different days.

7. The system of claim 1, wherein the instructions, when executed by the one or more processors, further cause the computing device to:
determine that a response to the alert message has not been received within a period of time for response; and
based on determining that the response to the alert message has not been received within the period of time for response, send a second alert message to a third computing device.

8. One or more non-transitory computer-readable media storing instructions that, when executed, cause:
receiving, from a gateway device, data indicating first internet data usage associated with a user device during a first time period;
determining that the first internet data usage is less than, by at least a threshold, second internet data usage associated with the user device during a second time period, wherein the second time period occurs prior to the first time period; and
based on the determining that the first internet data usage is less than, by at least the threshold, the second internet data usage, sending an alert message to a computing device.

9. The one or more non-transitory computer-readable media of claim 8, wherein the second internet data usage comprises one or more of internet activity associated with the user device or application software activity associated with the user device.

10. The one or more non-transitory computer-readable media of claim 8, wherein:
the second internet data usage comprises activation of a display device associated with the user device during the second time period, and
the instructions, when executed, cause the determining by determining that the display device was not activated during the first time period.

11. The one or more non-transitory computer-readable media of claim 8, wherein:
the second internet data usage comprises signing on to a service provider account associated with the user device during the second time period, and
the instructions, when executed, cause the determining by determining that a sign on to the service provider account did not occur during the first time period.

12. The one or more non-transitory computer-readable media of claim 8, wherein the instructions, when executed, cause the determining by determining that data has not been accessed by the user device within the first time period.

13. The one or more non-transitory computer-readable media of claim 8, wherein the first time period and the second time period occur during a common time range on different days.

14. The one or more non-transitory computer-readable media of claim 8, wherein the instructions, when executed, further cause:
determining that a response to the alert message has not been received within a period of time for response; and
based on the determining that the response to the alert message has not been received within the period of time for response, sending a second alert message to a second computing device.

15. A system comprising:
a first computing device; and
a second computing device,
wherein the first computing device comprises:
one or more first processors; and
first memory storing first instructions that, when executed by the one or more first processors, cause the first computing device to:
receive data indicating first application usage associated with a user device during a first time period;
compare the first application usage with second application usage associated with the user device during a second time period, wherein the second time period occurs prior to the first time period;
based on comparing the first application usage with the second application usage, determine that the first application usage is less than, by at least a threshold, the second application usage; and
based on determining that the first application usage is less than, by at least the threshold, the second application usage, send an alert message to the second computing device, and
wherein the second computing device comprises:
one or more second processors; and
second memory storing second instructions that, when executed by the one or more second processors, cause the second computing device to:
receive the alert message.

16. The system of claim 15, wherein the second application usage comprises one or more of:
television consumption activity associated with the user device, or
internet activity associated with the user device.

17. The system of claim 15, wherein:
the second application usage comprises activation of a display device of the user device, and
the first instructions, when executed by the one or more first processors, cause the first computing device to determine that the first application usage is less than, by at least the threshold, the second application usage by determining that the display device was not activated during the first time period.

18. The system of claim 15, wherein:
the second application usage comprises signing on to a service provider account associated with the user device, and
the first instructions, when executed by the one or more first processors, cause the first computing device to determine that the first application usage is less than, by at least the threshold, the second application usage by determining that a sign on to the service provider account associated with the user device did not occur during the first time period.

19. The system of claim 15, wherein the first instructions, when executed by the one or more first processors, cause the first computing device to determine that the first application usage is less than, by at least the threshold, the second application usage by determining that data has not been accessed by the user device within the first time period.

20. The system of claim 15, wherein the first instructions, when executed by the one or more first processors, cause the first computing device to send the alert message by sending, to the second computing device, a notification of an anomaly associated with the user device.

21. The system of claim 15, wherein the first instructions, when executed by the one or more first processors, cause the first computing device to:
determine that a response to the alert message has not been received within a period of time for response; and
based on determining that the response to the alert message has not been received within the period of time for response, send a second alert message to a third computing device.

22. One or more non-transitory computer-readable media storing instructions that, when executed, cause:
receiving data indicating first application usage associated with a user device during a first time period;
comparing the first application usage with second application usage associated with the user device during a second time period, wherein the second time period occurs prior to the first time period;
based on the comparing, determining that the first application usage is less than, by at least a threshold, the second application usage; and
based on the determining that the first application usage is less than, by at least the threshold, the second application usage, sending an alert message to a computing device.

23. The one or more non-transitory computer-readable media of claim 22, wherein the second application usage comprises one or more of:
television consumption activity associated with the user device, or
internet activity associated with the user device.

24. The one or more non-transitory computer-readable media of claim 22, wherein:
the second application usage comprises activation of a display device of the user device, and
the instructions, when executed, cause the determining by determining that the display device was not activated during the first time period.

25. The one or more non-transitory computer-readable media of claim 22, wherein:
the second application usage comprises signing on to a service provider account associated with the user device, and
the instructions, when executed, cause the determining by determining that a sign on to the service provider account associated with the user device did not occur during the first time period.

26. The one or more non-transitory computer-readable media of claim 22, wherein the instructions, when executed, cause the determining by determining that data has not been accessed by the user device within the first time period.

27. The one or more non-transitory computer-readable media of claim 22, wherein the instructions, when executed, cause the sending by sending, to the computing device, a notification of an anomaly associated with the user device.

28. The one or more non-transitory computer-readable media of claim 22, wherein the instructions, when executed, cause:
determining that a response to the alert message has not been received within a period of time for response; and
based on the determining that the response to the alert message has not been received within the period of time for response, sending a second alert message to a second computing device.

29. A system comprising:
a gateway device configured to send data indicating first video viewing associated with a user device during a first time period; and
a computing device, wherein the computing device comprises:
one or more processors; and
memory storing instructions that, when executed by the one or more processors, cause the computing device to:
receive, from the gateway device, the data;
determine that the first video viewing is less than, by at least a threshold, second video viewing associated with the user device during a second time period, wherein the second time period occurs prior to the first time period; and
based on determining that the first video viewing is less than, by at least the threshold, the second video viewing, send an alert message to a second computing device.

30. The system of claim 29, wherein the first video viewing comprises one or more of accessing television data, accessing online data, or accessing application data.

31. The system of claim 29, wherein:
the second video viewing comprises activation of a display device associated with the user device, and
the instructions, when executed by the one or more processors, cause the computing device to determine that the first video viewing is less than, by at least the threshold, the second video viewing by determining that the display device was not activated during the first time period.

32. The system of claim 29, wherein:
the second video viewing comprises signing on to a service provider account associated with the user device, and
the instructions, when executed by the one or more processors, cause the computing device to determine that the first video viewing is less than, by at least the threshold, the second video viewing by determining that a sign on to the service provider account associated with the user device did not occur during the first time period.

33. The system of claim 29, wherein the instructions, when executed by the one or more processors, cause the computing device to determine that the first video viewing is less than, by at least the threshold, the second video viewing by determining that data has not been accessed by the user device within the first time period.

34. The system of claim 29, wherein the instructions, when executed by the one or more processors, cause the computing device to:
determine that a response to the alert message has not been received within a period of time for response; and
based on determining that the response to the alert message has not been received within the period of time for response, send a second alert message to a third computing device.

35. One or more non-transitory computer-readable media storing instructions that, when executed, cause:
receiving, from a gateway device, data indicating first video viewing associated with a user device during a first time period;
determining that the first video viewing is less than, by at least a threshold, second video viewing associated with the user device during a second time period, wherein the second time period occurs prior to the first time period; and
based on the determining that the first video viewing is less than, by at least the threshold, the second video viewing, sending an alert message to a computing device.

36. The one or more non-transitory computer-readable media of claim 35, wherein the first video viewing comprises one or more of accessing television data, accessing online data, or accessing application data.

37. The one or more non-transitory computer-readable media of claim 35, wherein:
the second video viewing comprises activation of a display device associated with the user device, and
the instructions, when executed, cause the determining by determining that the display device was not activated during the first time period.

38. The one or more non-transitory computer-readable media of claim 35, wherein:
the second video viewing comprises signing on to a service provider account associated with the user device, and
the instructions, when executed, cause the determining by determining that a sign on to the service provider account associated with the user device did not occur during the first time period.

39. The one or more non-transitory computer-readable media of claim 35, wherein the instructions, when executed, cause the determining by determining that data has not been accessed by the user device within the first time period.

40. The one or more non-transitory computer-readable media of claim 35, wherein the instructions, when executed, further cause:
determining that a response to the alert message has not been received within a period of time for response; and
based on the determining that the response to the alert message has not been received within the period of time for response, sending a second alert message to a second computing device.

* * * * *